US012057243B2

(12) United States Patent
Vekselman et al.

(10) Patent No.: US 12,057,243 B2
(45) Date of Patent: Aug. 6, 2024

(54) SYSTEMS, DEVICES, AND METHODS FOR BEAM POSITION MONITORING AND BEAM IMAGING

(71) Applicant: TAE TECHNOLOGIES, INC., Foothill Ranch, CA (US)

(72) Inventors: Vladislav Vekselman, Lake Forest, CA (US); Alexander Dunaevsky, Corona, CA (US)

(73) Assignee: TAE TECHNOLOGIES, INC., Foothill Ranch, CA (US)

( * ) Notice: Subject to any disclaimer, the term of this patent is extended or adjusted under 35 U.S.C. 154(b) by 0 days.

(21) Appl. No.: 17/006,397

(22) Filed: Aug. 28, 2020

(65) Prior Publication Data

US 2021/0166832 A1 Jun. 3, 2021

Related U.S. Application Data

(60) Provisional application No. 63/065,442, filed on Aug. 13, 2020, provisional application No. 63/065,448, (Continued)

(51) Int. Cl.
*G21K 5/04* (2006.01)
*G01T 3/00* (2006.01)
*A61N 5/10* (2006.01)

(52) U.S. Cl.
CPC ............... *G21K 5/04* (2013.01); *G01T 3/00* (2013.01); *A61N 5/1075* (2013.01)

(58) Field of Classification Search
CPC .......... G21K 5/04; G01T 3/00; A61N 5/1075; A61N 5/1048; A61N 2005/109
See application file for complete search history.

(56) References Cited

U.S. PATENT DOCUMENTS

| 4,661,710 A | 4/1987 | Verney et al. |
| 4,782,304 A | 11/1988 | Aitken |

(Continued)

FOREIGN PATENT DOCUMENTS

| EP | 2612692 A1 | 7/2013 |
| JP | 59-171181 | 6/1986 |

(Continued)

OTHER PUBLICATIONS

International Search Report and Written Opinion for PCT/US2020/048416 (ISA/US) mailed Apr. 8, 2021 (16 pages).
International Search Report and Written Opinion for PCT/US2020/048443 (ISA/US) mailed Jan. 5, 2021 (25 pages).
WIPO Application No. PCT/US2020/048416, PCT International Preliminary Report on Patentability of the International Searching Authority mailed Mar. 10, 2022.

(Continued)

*Primary Examiner* — Marcus H Taningco
(74) *Attorney, Agent, or Firm* — ALSTON & BIRD LLP

(57) ABSTRACT

Embodiments of systems, devices, and methods relate to fast beam position monitoring for detecting beam misalignment in a beam line. In an example, a fast beam position monitor includes a plurality of electrodes extending into an interior of a component of a beam line. The fast beam position monitor is configured to detect a position of a beam passing through the component of the beam line based on beam halo current. Embodiments of systems, devices, and methods further relate to noninvasively monitoring parameters of beams advancing along a beam line. In examples, gas is puffed into a pumping chamber along a beam line. One or more beam parameters are measured from fluorescence resulting from collisions of energetic beam particulates of a beam advancing through the beam line.

24 Claims, 9 Drawing Sheets

Related U.S. Application Data filed on Aug. 13, 2020, provisional application No. 62/894,290, filed on Aug. 30, 2019, provisional application No. 62/894,220, filed on Aug. 30, 2019.

(56) References Cited

U.S. PATENT DOCUMENTS

| | | | |
|---|---|---|---|
| 6,403,972 B1* | 6/2002 | Cucchetti | G21K 1/093 250/492.21 |
| 8,933,421 B2* | 1/2015 | Drees | A61N 5/1048 250/492.1 |
| 9,583,302 B2 | 2/2017 | Figueroa Saavedra et al. | |
| 9,818,573 B2 | 11/2017 | Abs et al. | |
| 10,525,285 B1* | 1/2020 | Friedman | A61N 5/00 |
| 2002/0180365 A1 | 12/2002 | Okamura et al. | |
| 2003/0048080 A1 | 3/2003 | Amemiya et al. | |
| 2003/0152186 A1 | 8/2003 | Jurczyk et al. | |
| 2003/0195582 A1 | 10/2003 | Mann | |
| 2006/0011866 A1 | 1/2006 | Cho | |
| 2006/0102856 A1* | 5/2006 | Matsuda | A61N 5/1048 250/492.22 |
| 2007/0164237 A1 | 7/2007 | Bernhardt | |
| 2007/0215459 A1 | 9/2007 | Krzeminski et al. | |
| 2009/0039256 A1* | 2/2009 | Fujii | A61N 5/1048 250/306 |
| 2009/0099513 A1 | 4/2009 | Birchard | |
| 2010/0059687 A1* | 3/2010 | Balakin | H05H 13/04 250/396 R |
| 2011/0058167 A1 | 3/2011 | Knox et al. | |
| 2011/0186746 A1 | 8/2011 | Drees et al. | |
| 2012/0080618 A1 | 4/2012 | Clayton et al. | |
| 2012/0135650 A1 | 5/2012 | Servante et al. | |
| 2013/0231517 A1* | 9/2013 | Iwamoto | A61N 5/1043 600/1 |
| 2014/0213867 A1 | 7/2014 | Pletcher et al. | |
| 2014/0296610 A1 | 10/2014 | Nishiuchi | |
| 2014/0320006 A1 | 10/2014 | Abs et al. | |
| 2015/0238780 A1* | 8/2015 | Nishimura | A61N 5/1075 600/2 |
| 2016/0064186 A1 | 3/2016 | Chang et al. | |
| 2016/0263402 A1 | 9/2016 | Zhang et al. | |
| 2017/0062086 A1 | 3/2017 | Park, Jr. et al. | |
| 2017/0135194 A1 | 5/2017 | Belchenko et al. | |
| 2017/0296844 A1* | 10/2017 | Trail | H01J 1/46 |
| 2020/0196428 A1 | 6/2020 | Ryding et al. | |

FOREIGN PATENT DOCUMENTS

| | | |
|---|---|---|
| JP | H08 23067 B2 | 3/1996 |
| JP | 2003-303569 A | 10/2003 |
| JP | 2009-32623 A | 2/2009 |
| JP | 2010-509714 A | 3/2010 |
| JP | 2015-217207 A | 12/2015 |
| RU | 2418338 C1 | 5/2011 |
| WO | WO 2018-168713 A1 | 9/2018 |

OTHER PUBLICATIONS

WIPO Application No. PCT/US2020/048443, PCT International Preliminary Report on Patentability of the International Searching Authority mailed Mar. 10, 2022.

Dudnikov et al., "High current density negative ion source for beam line transport studies," Proceedings of the 2001 Particcle Acelerator Conference, vol. 3, pp. 2090-2092, (Jun. 2001).

Ido et al., "Development of a Heavy Ion Beam Probe for Measuring Electrostatic Potential Profile and its Fluctuation in LHD," Plasma Science and Technology, Institute of Physics Publishing, vol. 11, No. 4, pp. 460-464, (Aug. 2009).

Kasatov et al., "Proton beam of 2 MeV 1.6 mA on a tandem accelerator with vacuum insulation," Journal of Instrumentation, Institute of Physics Publishing, vol. 9, No. 12, (Dec. 2014).

Kim et al., "Progress report of the innovated KIST ion beam facility," Nuclear Instruments & Methods in Physics Reasearch, Section B: Beam Interactions with Materials and Atoms, vol. 391, pp. 57-63, (Nov. 2016).

Kobayashi et al., "Current status of the AMS System at the University of Tokyo," Nuclear Instruments and Methods in Physics Research, Section B: Beam Interations with Materials and Atoms, vol. 123, No. 1-4, pp. 107-111, (Mar. 1997).

Mori et al., "Intense Negative Heavy Ion Source with Cusp Magnetic Field," Accelerator Science andTechnology, vol. 1 of 3, pp. 345-347, (Mar. 1989).

EP 20859978.7 Extended European Search Report mailed Aug. 25, 2023.

Bungau et al. "Target Optimisation Studies for the European Spallation Source," Proceedings of IPAC'210, Kyoto, Japan, pp. 256-258, (Jun. 2010).

Hassanzadegan et al., "System Overview and Current Status of the ESS Beam Position Monitors," Proceedings of the 5th International Particle Acelerator Conference, pp. 3653-3655, (Jul. 2014).

Hassanzadegan et al., "System Overview and Design Considerations of the BPM System of the ESS Linac," Proceeding of the 2nd International Beam Instrucmentation C onference, pp. 388-391, (Dec. 2013).

Kreiner et al., "A Tandem-electrostatic-quadrupole for accelerator-based BNCT," Nuclear Instruments and Methods in Physics Research, B 261, 751-754, (Apr. 2007).

EP 20859978.7 Extended European Search Report mailed Sep. 22, 2023.

RU Application No. 2022107821, Search Report mailed Apr. 15, 2024.

U.S. Appl. No. 17/984,954, Notice of Allowance mailed Apr. 17, 2024.

Taskaev et al., "Vacuum-Insulation Tandem Accelerator for oron Neutron Capture Theraply," Proceedings of IPAC2011, Switzerland, CERN, Sep. 2011, pp. 3615-3617.

* cited by examiner

SYSTEMS, DEVICES, AND METHODS FOR BEAM POSITION MONITORING AND BEAM IMAGING

CROSS-REFERENCE TO RELATED APPLICATIONS

The present application claims priority to U.S. Provisional Application Ser. No. 63/065,448, titled "SYSTEMS, DEVICES, AND METHODS FOR FAST BEAM POSITION MONITORING," filed Aug. 13, 2020, and to U.S. Provisional Application Ser. No. 63/065,442, titled "SYSTEMS, DEVICES, AND METHODS FOR GAS PUFF BEAM IMAGING," filed Aug. 13, 2020, and to U.S. Provisional Application Ser. No. 62/894,290, titled "SYSTEMS, DEVICES, AND METHODS FOR FAST BEAM POSITION MONITORING," filed Aug. 30, 2019, and to U.S. Provisional Application Ser. No. 62/894,220, titled "SYSTEMS, DEVICES, AND METHODS FOR GAS PUFF BEAM IMAGING," filed Aug. 30, 2019, all of which are incorporated by reference herein in their entirety.

FIELD

The subject matter described herein relates generally to beam systems and, in particular, to beam diagnostics of the charged particle beamline of the beam system, and, further in particular, systems and methods for facilitating fast beam position monitoring for detection of beam misalignment in the beamline. The subject matter further relates to systems and methods for facilitating non-invasive beam diagnostics.

BACKGROUND

Boron neutron capture therapy (BNCT) is a modality of treatment of a variety of types of cancer, including some of the most difficult types. BNCT is a technique that selectively aims to treat tumor cells while sparing the normal cells using a boron compound. A substance that contains boron is injected into a blood vessel, and the boron collects in tumor cells. The patient then receives radiation therapy with neutrons (e.g., in the form of a neutron beam). The neutrons react with the boron to kill the tumor cells while reducing or eliminating harm to normal cells. Prolonged clinical research has proven that a beam of neutrons with an energy spectrum within 3-30 kiloelectronvolts (keV) may be preferable to achieve a more efficient cancer treatment while decreasing a radiation load on a patient. This energy spectrum or range is frequently referred to as epithermal.

Most conventional methods for the generation of epithermal neutrons (e.g., epithermal neutron beams) are based on nuclear reactions of protons (e.g., a proton beam) with either beryllium or lithium (e.g., a beryllium target or a lithium target).

For solutions based on electrostatic accelerators, beam diagnostics is an intrinsic part of the charged particle beamline design. A critical task in beam transport is to ensure that the beam is correctly positioned inside the beamline (e.g., there is no direct beam interaction with beamline components and walls). Any impact of placement or use of such beam diagnostics can be proportional to the beam energy as the beam destructive power goes up with beam energy. This is especially true for the transport of direct current (DC) beams where irreversible damage to the beamline components can be created at millisecond time scale. Therefore, continuous monitoring of the beam position is a key to success with the beam transport in accelerator based solutions.

A conventional beam position monitor (BPM) based on arrays of secondary emission monitors demonstrates reliable operation with millimeter resolution. However, the conventional BPM has a relatively low beam power acceptance threshold due to direct interaction of its probes (thin foils) with the beam. Accordingly, beam monitoring based on arrays of secondary emission monitors is not preferred for beams up to 3.5 megawatts (MW).

Non-destructive beam position monitors (BPMs) are typically based on detection of beam impedance. Such non-destructive BPMs are mostly capacitive type BPMs (e.g., linear-cut, button types, and stripline BPMs). The principle of operation of such beam impedance detection devices results in their use being limited to pulsed beams.

Conventional systems appear 1) unable to successfully operate with DC beams, 2) to lack a millisecond response time, 3) to be unable to accept beams having power up to 2.5 megaelectronvolts (MeV) per nuclei, 4) to lack simplicity, and 5) to lack reliability.

For accelerator based solutions, the deliverables of such beam diagnostics also include providing information about beam parameters and characteristics which are extensively d for arrangement and control of beamline elements, beam shaping, beam focusing, beam bending, cleaning and rotation or beamline elements, beam monitoring and statistics, and more. Conventionally, the most developed and utilized beam diagnostics are what may be referred to as invasive diagnostics whose effect on the beam (e.g., during the process of measurement) commonly results in undesired perturbation of one or more beam parameters.

Conventional invasive beam diagnostics for measuring beam size and cross-sectional profile include slit grid and Allison emittance scanners, wire beam profilers, and the like. However, such invasive beam diagnostics are not well suited for real time beam tracking because they a) perturb the beam in a way that typically results in undesired termination of the beam after a short duration, and b) are limited in terms of acceptable beam power due to direct interaction with the beam particulates.

The use of a conventional beam wire scanner is limited by the probe collected beam power. Therefore, a direct current (DC) beam can only be probed in the region of the low beam energy (e.g., 30 kiloelectronvolts (keV) in a relatively low energy beamline at 15 milliamps (mA) current). To overcome this limitation, a pulsed beam can be used that allows the use of a wire scanner with beams of higher energy (determined by the beam pulse duration). However, both approaches (e.g., with or without a pulsed beam) are not suitable for continuous monitoring of the beam parameters (location and size) because of beam distortion during the measurements.

It is important to note that interaction of the energetic beam particulates with a probe is typically accompanied by various phenomena, some of which may drastically complicate signal interpretation. For example, secondary electron emission (SEE) phenomenon modifies the current measured on a probe (the signal). The common approach of SEE suppression via probe biasing does not ensure diminishing the SEE contribution into the signal for arbitrary energy of beam particulates. Furthermore, possible plasma formation near the probe surface and rapid heating of the probe are processes affecting the signal as well. The contributions of these phenomena are difficult to predict and account for.

To monitor high power DC beams (up to 5 kilowatts (kW)) and deliver basic beam characteristics such as beam position, size, and profile, a truly non-invasive beam diagnostics is desirable. In addition, availability of such non-invasive beam diagnostics may facilitate a real-time feedback loop for beam control systems.

For these and other reasons, a need exists for improved, efficient, and compact systems, devices, and methods that monitor beam position within a beam system as well as improved, efficient, and compact systems, devices, and methods that provide non-invasive beam diagnostics within a neutron beam system.

SUMMARY

Example embodiments of systems, devices, and methods are described herein for beam systems, and, more particularly, systems and methods for facilitating fast beam position monitoring for detection of beam misalignment in a beamline. In certain example embodiments, a beam position monitor (BPM) (e.g., also referred to herein as a fast beam position monitor or FBPM) is provided for an example beam system configured as a neutron beam systems (NBS).

In certain example embodiments, the beam position monitor (BPM) can include multiple electrodes extending into the interior of the beamline of the beam system. In these embodiments, the beam position monitor (BPM) can operate by collection of the beam halo current by the electrodes. The electrodes can be galvanically isolated from a wall of the BPM and biased using an external power supply. Biasing relative to the BPM wall can reduce contribution of secondary electron emission (SEE) current to the signal and can increase the beam halo current collected from the beam generated plasma.

The beam position monitor (BPM) can include a detection sensitivity level associated with reducing or eliminating beam-induced damage to beamline components while minimizing disturbance to the beam advancing through the beam line. That is, a minimal amount of a beam current of the beam passing through the component of the beam line can be reduced due to the electrodes.

Embodiments of systems, devices, and methods further relate to accelerator based beam systems and, more particularly, systems and methods for facilitating non-invasive beam diagnostics. In example embodiments, a non-invasive beam diagnostics system includes a gas puff beam imaging (GPBI) diagnostics system suitable for a beamline, for example a beamline serving as part of a neutron beam system (NBS). The gas puff beam imaging (GPBI) diagnostics system can be adapted to deliver information about the beam position and size in real time without substantial beam perturbation. The non-invasive beam diagnostics system is time-resolved and space-resolved and works for wide ranges of different beam powers. Moreover, the present gas puff beam imaging (GPBI) diagnostics system is suitable for a high energy beamline (HEBL), or in or near a tandem accelerator as part of a neutron beam system (NB S).

Example embodiments overcome the aforementioned limitations associated with conventional invasive beam monitoring solutions by enabling non-invasive continuous monitoring of the beam and acquisition of critical beam parameters (size, location, profile) for a beam control system without restrictions on the upper limit of the beam power. In addition, both temporal and spatial resolution of the present GPBI diagnostics system is improved over conventional diagnostics. For example, the time resolution of the present GPBI diagnostics system is approximately hundreds of milliseconds, which is a significant improvement over the measurement timescale of the wire scanners (several seconds).

In example embodiments, the fluorescence of residual (background) or puffed gases produced due to collisions with energetic beam particulates is used as part of a non-destructive diagnostic technique for measuring transverse beam sizes (profiles) and beam position. To measure beam parameters (e.g., transverse size, location, inclination), a glow of fluorescence from the beam-gas interaction region is recorded by recording devices or imaging components (e.g., cameras) of beam imaging diagnostics providing data on beam transversal size, beam location, and inclination.

Other systems, devices, methods, features and advantages of the subject matter described herein will be or will become apparent to one with skill in the art upon examination of the following figures and detailed description. It is intended that all such additional systems, methods, features and advantages be included within this description, be within the scope of the subject matter described herein and be protected by the accompanying claims. In no way should the features of the example embodiments be construed as limiting the appended claims, absent express recitation of those features in the claims.

BRIEF DESCRIPTION OF FIGURES

The details of the subject matter set forth herein, both as to its structure and operation, may be apparent by study of the accompanying figures, in which like reference numerals refer to like parts. The components in the figures are not necessarily to scale, emphasis instead being placed upon illustrating the principles of the subject matter. Moreover, all illustrations are intended to convey concepts, where relative sizes, shapes and other detailed attributes may be illustrated schematically rather than literally or precisely.

DETAILED DESCRIPTION

Before the present subject matter is described in detail, it is to be understood that this disclosure is not limited to the particular embodiments described, as such may, of course, vary. It is also to be understood that the terminology used herein is for the purpose of describing particular embodiments only, and is not intended to be limiting, since the scope of the present disclosure will be limited only by the appended claims.

The term "particle" is used broadly herein and, unless otherwise limited, can be used to describe an electron, a proton (or H+ ion), or a neutral, as well as a species having more than one electron, proton, and/or neutron (e.g., other ions, atoms, and molecules).

Example embodiments of systems, devices, and methods are described herein for diagnostics in a beam system (e.g., including a particle accelerator). The embodiments described herein can be used with any type of particle accelerator or in any particle accelerator application involving production of a charged particle beam at specified energies for supply to the particle accelerator. Embodiments herein can be used in numerous applications, an example of which is as a neutron beam system for generation of a neutron beam for use in boron neutron capture therapy (BNCT). For ease of description, many embodiments described herein will be done so in the context of a neutron beam system for use in BNCT, although the embodiments are not limited to just the generation of neutron beams nor BNCT applications in particular.

Figure 1A:
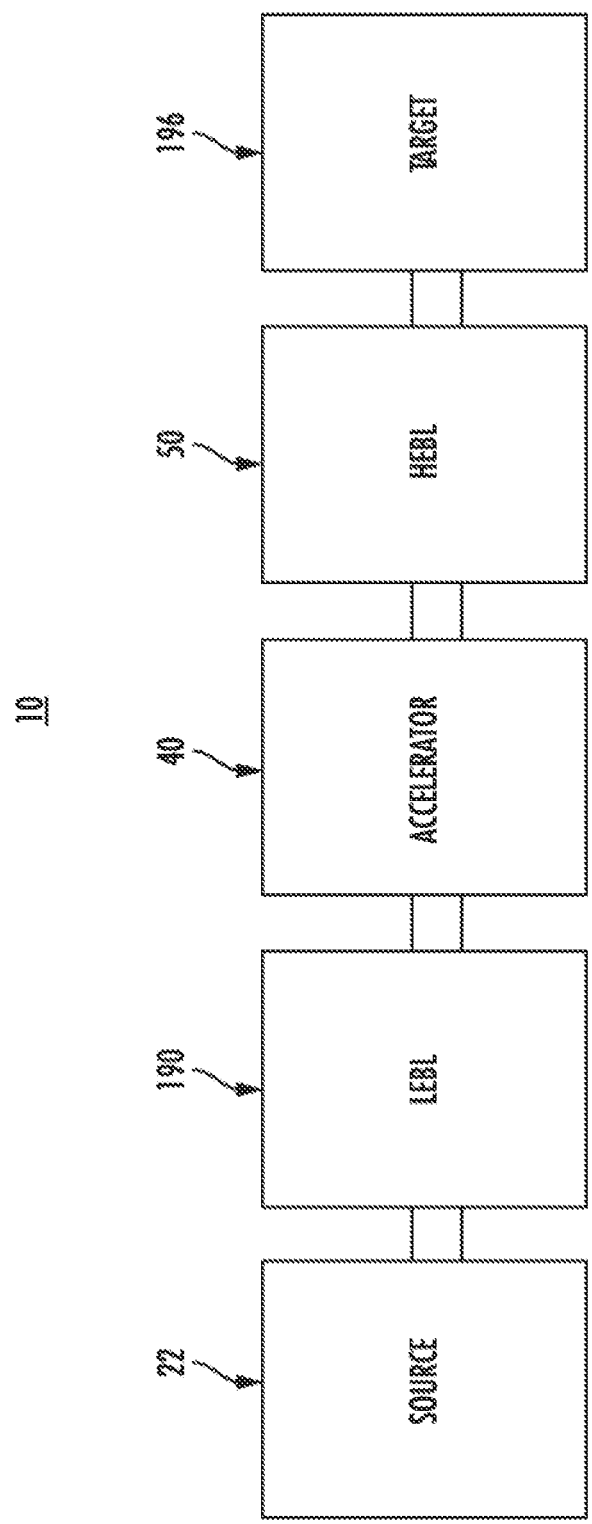
FIG. 1A is a schematic diagram of an example embodiment of a neutron beam system for use with embodiments of the present disclosure.

FIG. 1A is a schematic diagram of an example embodiment of a beam system for use with embodiments of the present disclosure. Here, beam system 10 includes a source 22, a low-energy beamline (LEBL) 190, an accelerator 40 coupled to the low-energy beamline (LEBL) 190, and a high-energy beamline (HEBL) 50 extending from accelerator 40 to a target assembly housing a target 196. LEBL 190 is configured to transport a beam from source 22 to accelerator 40, which is configured to accelerate the beam HEBL 50 transfers the beam from an output of accelerator 40 to a target 196.

Example embodiments of systems, devices, and methods are described herein for facilitating fast beam position monitoring for detection of beam misalignment in a beamline of a beam system 10. In example embodiments, a simple and reliable beam position monitor (BPM) is provided. In certain example embodiments, the beam position monitor (BPM) can include multiple electrodes extending into the interior of the beamline of the neutron beam system (NBS). In these embodiments, the beam position monitor (BPM) can operate by collection of the beam halo current by the electrodes. The electrodes can be galvanically isolated from a wall of the BPM and biased using an external power supply. Biasing relative to the BPM wall can reduce contribution of secondary electron emission (SEE) current to the signal and can increase the beam halo current collected from the beam generated plasma.

In example embodiments, the beam position monitor (BPM) is configured to signal or indicate to a control system when a beam advancing through the beam line is off axis.

The beam position monitor (BPM) can include a detection sensitivity level associated with reducing or eliminating beam-induced damage to beamline components while minimizing disturbance to the beam advancing through the beam line. That is, a minimal amount of a beam current of the beam passing through the component of the beam line can be reduced as a result of current collection by the electrodes. Example embodiments of the BPM can advantageously operate with direct current (DC) beams, have millisecond (or faster) response time, and/or accept beam powers of 2.5 MeV (and higher) per nuclei.

In some example embodiments, the BPM can be part of a beam system configured for producing a neutron beam from a ion beam. The beam system can include an LEBL, serving as an ion beam injector system, a high voltage (HV) tandem accelerator coupled to the ion beam injector system, and an HEBL extending from the tandem accelerator to a neutron target assembly housing a neutron-producing target. In these example embodiments, the ion beam injector can include an ion source, beam optics incorporated into a low-energy beamline extending from the ion source, a pre-accelerator tube, beam diagnostics and a pumping chamber coupled to the tandem accelerator. The ion source can generate charged particles in the plasma volume which can be extracted, accelerated, conditioned and eventually used to produce neutrons when delivered to the neutron producing target. Such improved, efficient, and compact systems, devices, and methods that monitor the beam position enable preservation of neutron beam system equipment while maintaining operative efficacy.

System 10 can also include a gas based or substantially non-invasive beam diagnostics system. This diagnostics system can include gas puff beam imaging (GPBI) suitable for the LEBL, serving as the beam injector of the beam system, where the GPBI is adapted to deliver information about the beam position and size in real time without beam perturbation. Moreover, the present GPBI diagnostics system is suitable for a high energy beamline (HEBL), or in or near the accelerator. The non-invasive beam diagnostics system is time-and space-resolved and has no upper limit on the beam power.

In example embodiments, the fluorescence of residual (background) or puffed gases produced due to collisions with energetic beam particulates is used as part of a non-destructive diagnostic technique for measuring transverse beam sizes (profiles) and beam position. The propagation of charged particles through a gas environment leads to the emission of light due to collisional excitation of gas atoms and molecules. To measure beam parameters (transverse size, location, inclination), the glow of fluorescence from the beam-gas interaction region is recorded by recording devices or imaging components (e.g., cameras) providing data on beam transversal size, beam location and inclination. Obtained images can be further correlated with the actual beam profile via Abel inversion (under certain assumptions, e.g., beam axial symmetry) or using tomographic techniques.

In example embodiments, a GPBI diagnostics system includes one or more imaging components, and in many embodiments at least two (2) orthogonally oriented imaging components, coupled to and extending into an interior of a pumping chamber and a gas puff port extending from the pumping chamber and providing a passage into the pumping chamber.

The gas puff port is controllable such that a number of neutrals introduced into the GPBI diagnostics system is regulated to avoid interaction with the beam that is to be measured or observed. That is, the beam passing through the beamline, while being observed by the GPBI diagnostics system, passes through a cloud of neutrals without being substantially disturbed. In embodiments, the gas puffed in embodiments of the present disclosure comprises one or more of argon or xenon.

Figure 1B:
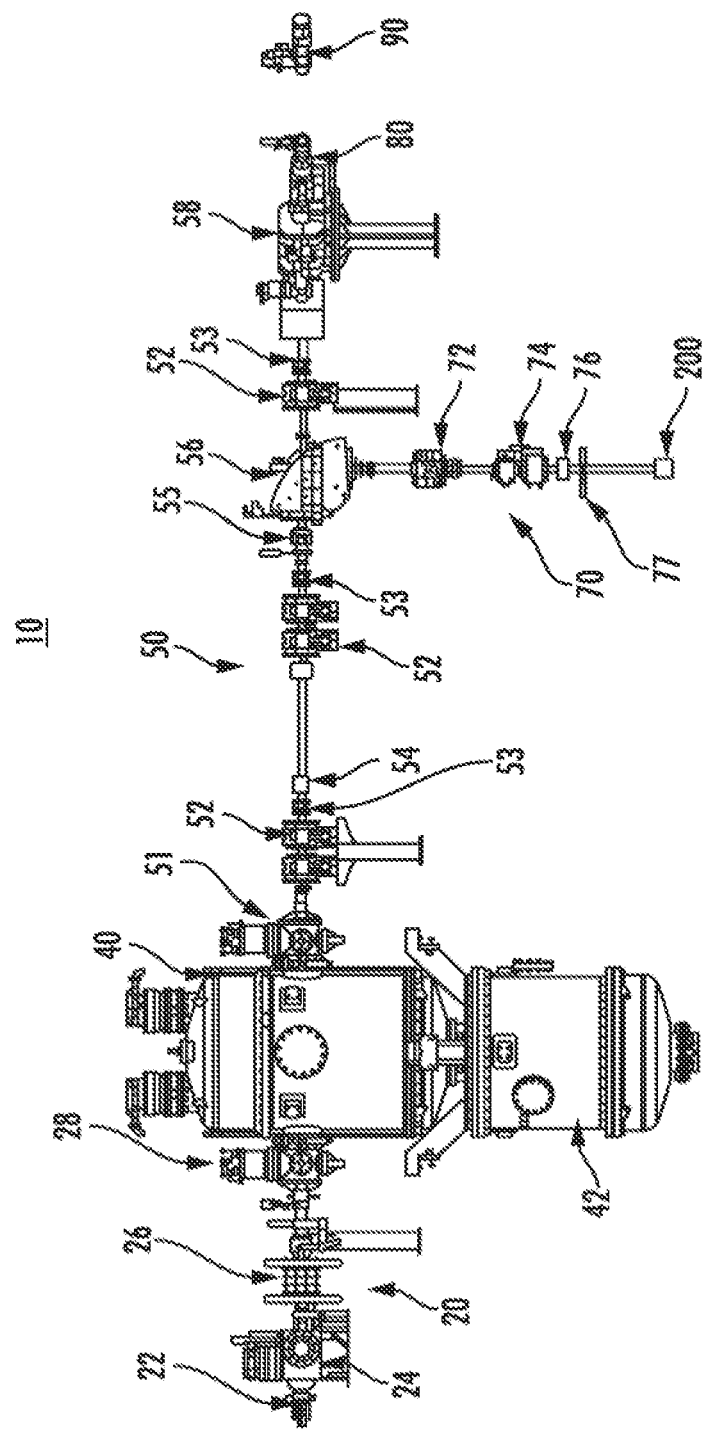
FIG. 1B is a schematic diagram of an example embodiment of a neutron beam system for use in boron neutron capture therapy (BNCT).
Figure 2:
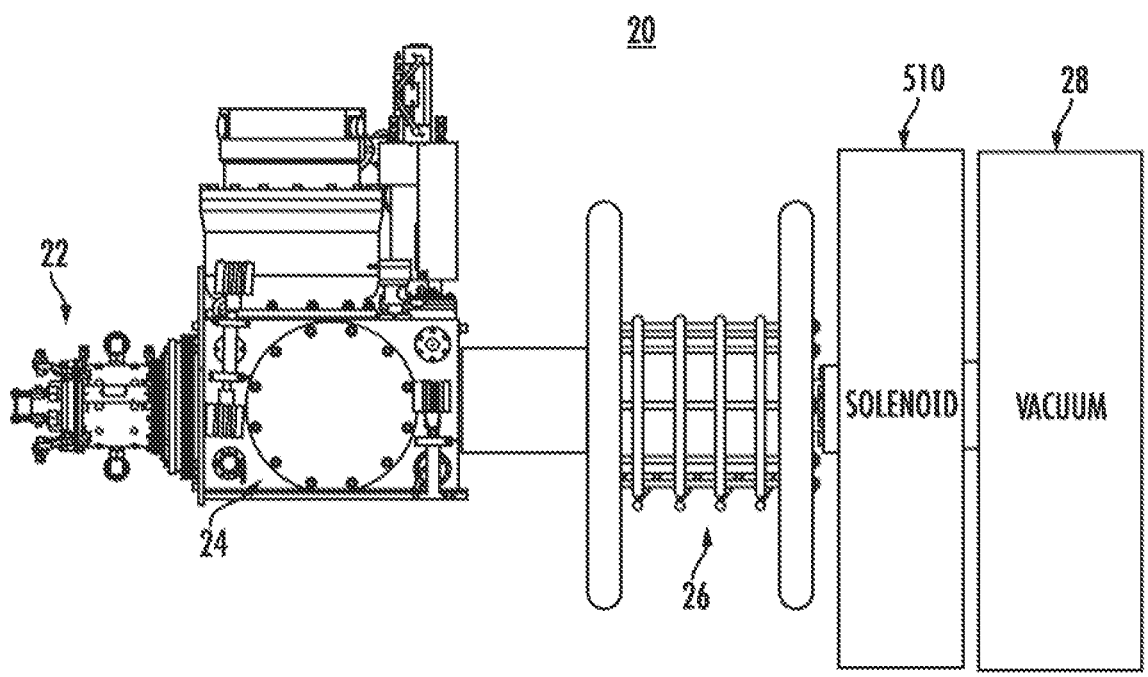
FIG. 2 illustrates an example pre-accelerator system or ion beam injector for use with embodiments of the present disclosure.

FIG. 1B is a schematic diagram illustrating an example neutron beam system 10 for use in boron neutron capture therapy (BNCT), according to embodiments of the present disclosure. The neutron beam system 10 includes a pre-accelerator system 20 forming at least a portion of the LEBL, where the pre-accelerator system 20 serves as a charged particle beam injector as shown in FIG. 2, a high voltage (HV) tandem accelerator 40 coupled to the pre-accelerator system 20, and a high-energy beamline 50 extending from the tandem accelerator 40 to a neutron target assembly 200 housing the neutron-producing target. In this embodiment beam source 22 is an ion source and the charged particle beam is a negative ion beam prior to conversion to a proton beam within tandem accelerator 40. It will be appreciated that neutron beam system 10 as well as pre-accelerator system 20 can also be used for other applications, such as cargo inspection and others, and is not limited to BNCT.

Pre-accelerator system 20 (also referred to herein as the charged particle beam injector or ion beam injector) is configured to transfer the ion beam from the ion source 22 to the input (e.g., an input aperture) of the tandem accelerator 40.

Tandem accelerator 40, which is powered by a high voltage power supply 42 coupled thereto, can, in many embodiments, produce a proton beam with an energy generally equal to twice the voltage applied to the accelerating electrodes positioned within the tandem accelerator 40. The energy level of the proton beam is achieved by accelerating the beam of negative hydrogen ions from the input of the tandem accelerator 40 to the innermost high-potential electrode, stripping two electrons from each ion, and then accelerating the resulting protons downstream by the same voltages encountered in reverse order.

The high-energy beamline 50 transfers the proton beam from the output of the tandem accelerator 40 to the neutron-generating target in the neutron target assembly 200 positioned at the end of a branch 70 of the beamline extending into a patient treatment room. System 10 can be configured to direct the proton beam to any number of one or more targets and associated treatment areas. In this embodiment, the high-energy beamline 50 includes three branches 70, 80 and 90 to extend into three different patient treatment rooms. The high-energy beamline 50 includes a pumping chamber 51, quadrupole magnets 52 and 72 to prevent de-focusing of the beam, dipole or bending magnets 56 and 58 to steer the beam into treatment rooms, beam correctors 53, diagnostics such as current monitors 54 and 76, fast beam position monitor 55 section, and a scanning magnet 74.

The design of the high-energy beamline 50 may depend on the configuration of the treatment facility (e.g., a single-story configuration of a treatment facility, a two-story configuration of a treatment facility, and the like). The beam can be delivered to a target assembly (e.g., positioned near a treatment room) 200 with the use of the bending magnet 56. Quadrupole magnets 72 can be included to then focus the beam to a certain size at the target. Then, the beam passes one or more scanning magnets 74, which provides lateral movement of the beam onto the target surface in a desired pattern (e.g., spiral, curved, stepped in rows and columns, combinations thereof, and others). The beam lateral movement can help achieve smooth and even time-averaged distribution of the proton beam on the lithium target, preventing overheating and making the neutron generation as uniform as possible within the lithium layer.

After entering the scanning magnets 74, the beam can be delivered into a current monitor 76, which measures beam current. The measured beam current value can be used to operate a safety interlock. The target assembly 200 can be physically separated from the high energy beamline volume with a gate valve 77. The main function of the gate valve is separation of the vacuum volume of the beamline from the target while target exchange/loading. In embodiments, the beam may not be bent by 90 degrees by a bending magnet 56, it rather goes straight to the right, then it enters the quadrupole magnets 52, which are located in the horizontal beamline. After, the beam could be bent by another bending magnet 58 to a needed angle, depending on the room configuration. Otherwise, the bending magnet 58 could be replaced with a Y-shaped magnet in order to split the beamline into two directions for two different treatment rooms located on the same floor.

FIG. 2 illustrates an example of a pre-accelerator system or ion beam injector for use with embodiments of the present disclosure. In this example, pre-accelerator system 20 includes an einzel lens (not shown), a pre-accelerator tube 26, and a solenoid 510, and is configured to accelerate a negative ion beam injected from ion source 22. The pre-accelerator system 20 is configured to provide acceleration of the beam particles to the energies required for tandem accelerator 40, and to provide overall convergence of the negative ion beam to match input aperture area at an input aperture or entrance of the tandem accelerator 40. The pre-accelerator system 20 is further configured to minimize or defocus backflow as it passes from the tandem accelerator 40 through the pre-accelerator system in order to reduce the possibility of damage to ion source and/or the backflow reaching the filaments of the ion source.

In embodiments, the ion source 22 is configured to provide a negative ion beam downstream to the einzel lens (not shown), and the negative ion beam continues to pass through pre-accelerator tube 26 and a solenoid 510. The solenoid 510 is positioned between the pre-accelerator tube the tandem accelerator and is electrically couplable with a power supply. The negative ion beam passes through the solenoid 510 to the tandem accelerator 40.

Pre-accelerator system 20 can also include an ion source vacuum box 24, and a pumping chamber 28, which, with pre-accelerator tube 26 as well as the other elements described above are part of a relatively low energy beamline leading to the tandem accelerator 40. The ion source vacuum box 24, within which the einzel lens (not shown) is positioned, extends from the ion source 22. The pre-accelerator tube 26 can be coupled to the ion source vacuum box 24, and solenoid 510 can be coupled to the pre-accelerator tube 26. A pumping chamber 28 can be coupled to the solenoid 510 and the tandem accelerator 40. The ion source 22 serves as a source of charged particles which can be accelerated, conditioned and eventually used to produce neutrons when delivered to a neutron producing target. The example embodiments will be described herein with reference to an ion source producing a negative hydrogen ion beam, although embodiments are not limited to such, and other positive or negative particles can be produced by the source.

The pre-accelerator system 20 can have zero, one, or multiple magnetic elements for purposes such as focusing and/or adjusting alignment of the beam. For example, any such magnetic elements can be used to match the beam to the beamline axis and the acceptance angle of the tandem accelerator 40. The ion vacuum box 24 may have ion optics positioned therein.

There are two types of negative ion sources 22, which differ by the mechanism of generation of negative ions: the surface type and the volume type. The surface type generally requires the presence of cesium (Cs) on specific internal surfaces. The volume type relies on formation of negative ions in the volume of a high current discharge plasma. While both types of ion sources can deliver the desired negative ion current for applications related to tandem accelerators, surface type negative ion sources are undesirable for modulation. That is, for modulation of a negative ion beam in embodiments described herein, negative ion sources of the volume type (e.g., without employing cesium (Cs)) are preferred.

Figure 3:
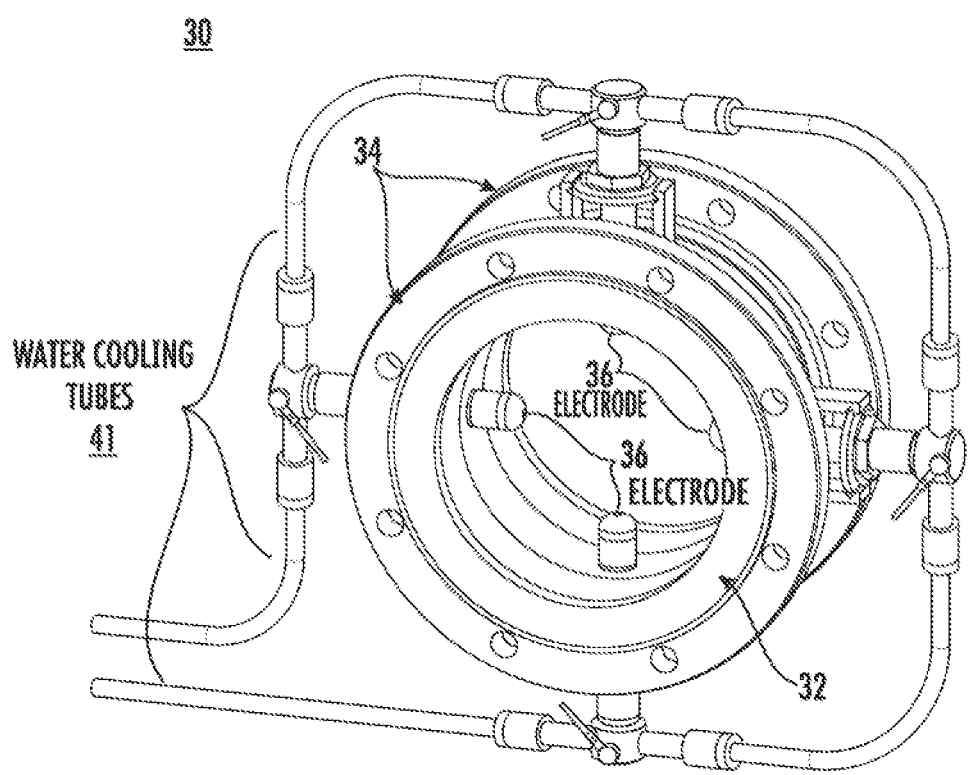
FIG. 3 is a perspective view of an example embodiment of a beam position monitor (BPM) of the ion beam injector system shown in FIG. 2.

Turning to FIG. 3, an example beam position monitor (BPM) (e.g., or fast beam position monitor) 30 includes a cylindrical wall 32 extending between a pair of flanges 34 adapted to mount the beam position monitor (BPM) 30 along the beam line (e.g., low energy beamline (LEBL) including pre-accelerator system 20, accelerator 40, high energy beamline (HEBL) 50). In examples where the beam position monitor (BPM) 30 is mounted along the low energy beamline (LEBL), the beam position monitor (BPM) may be mounted between the pre-accelerator tube 26 and pumping chamber 28. The operation of the beam position monitor (BPM) 30 may be based on collection of the beam halo current by electrodes 36 protruding from the wall 32 and extending into the interior of the beam line. In example embodiments, electrodes 36 may be cooled by way of one or more cooling devices 41. In example embodiments, the one or more cooling devices may comprise water cooling devices.

In FIG. 3, the beam position monitor (BPM) 30 is shown to include four electrodes 36, although embodiments are not limited to four electrodes (e.g., any number of electrodes may be employed within the scope of the present disclosure). The electrodes 36 are preferably shaped as cylinders and made of one or more of tantalum (Ta) or tungsten (W) to increase resistance to the heat flux. The electrodes 36 may also be made of composite materials that are able to withstand the thermal load generated by the beam. The insertion length (e.g., electrode extension distance into the interior of the beam line) of an electrode 36 can be adjusted separately for each electrode 36 (e.g., using a control system, not shown in FIG. 3), allowing a user to adapt the beam position monitor (BPM) 30 for beams of arbitrary dimensions. The electrodes 36 are intended to be exposed to the beam halo current, therefore the collected power flux is anticipated to be much lower. Moreover, the plasma formed near the region of the beam-residual gas interaction expands to the beam outer boundary forming an additional signal for the beam position monitor (BPM) 30.

Electrodes 36 can be galvanically isolated from the BPM wall 32 and biased using an external power supply. Biasing relative to the BPM wall 32 a) can reduce contribution of secondary electron emission (SEE) current to the signal and b) can increase the beam halo current collected from the beam generated plasma.

While the beam system is operating and a beam is being extracted from a source (e.g., 22) and propagated through components (e.g., 190, 40, 50, 196) of an example beam system g., 10), the beam position monitor (BPM) 30 enables a control system to actively monitor the beam position. Each electrode 36 may have associated with it a current threshold (e.g., a signal threshold). When collected current (e.g., or signal) by a given electrode exceeds its current threshold, the beam may be deemed to have deflected too far toward that electrode and, as such, be off axis. The beam position monitor (30) can provide an indication that current collected by the electrode has exceeded its current threshold to the control system, and the control system can adjust parameters of one or more components of the entire beam system (e.g., 10) to move the beam back on axis. Examples of adjustable parameters may include inputs provided to beam steering magnets such that positions of the beam steering magnets are altered to move the beam back onto the desired axis. In this manner, the beam position monitor (BPM) 30 along with the control system continuously/repeatedly and in real time provide feedback to the beam steering magnets and/or other components of the beam system.

In embodiments, a current threshold associated with a given electrode may be different from a current threshold associated with another electrode of the beam position monitor (30). Further, a given electrode may have associated with it multiple current thresholds for more granular detection of beam position. That is, multiple current thresholds can be used with the electrodes of the beam position monitor (e.g., 30). Detection of movement of the beam off axis in a direction between electrodes may be based on multiple current thresholds associated with adjacent electrodes.

For example, a pair of adjacent electrodes may both register an increase in signal level (e.g., current collected), however the increase in signal level may exceed a second, lower current threshold associated with each electrode of the pair of adjacent electrodes. In such an example, the signal level exceeding the second, lower current threshold associated with each electrode of the pair of adjacent electrodes may indicate that the beam is in an off axis direction between the electrodes.

Accordingly, the control system may adjust the beam steering magnets based on an indication that the signal level exceeds a single threshold for a single electrode of the beam position monitor (BPM) 30, or based on an indication that the signal level exceeds two lower thresholds for adjacent electrodes.

Moreover, the control system may monitor the magnitudes of signal on each of the electrodes and extrapolate a degree of beam deflection in a particular direction based on the magnitudes of the signal (e.g., independent of or in combination with one or more current thresholds associated with the electrodes). The control system may then adjust the beam steering magnets, or other parameters, based on the extrapolated degree(s) of beam deflection in order to compensate for the beam deflection and bring the beam back to its desired axis. In such examples, the control system can continuously and in real-time adjust beam line parameters, such as positions of the beam steering magnets, based on a minimum amount of detected deflection (e.g., a deflection threshold).

In examples, it may be difficult to predict the signal level on the BPM electrodes 36. Accordingly, calibration of the BPM 30 prior to operation may be desired and performed. Calibration may be accomplished by controllable and safe shifting of a beam off of the beamline axis and collecting the current on the BPM electrodes 36.

Pulsed mode of beam operation may be preferable during calibration of the BPM 30 to reduce the total beam deposited energy on the BPM 30 and other beam line components. Other beam position diagnostics (e.g., gas puff beam imaging) may also be involved in concert with the BPM calibration to meet safety or other regulations.

Figure 4:
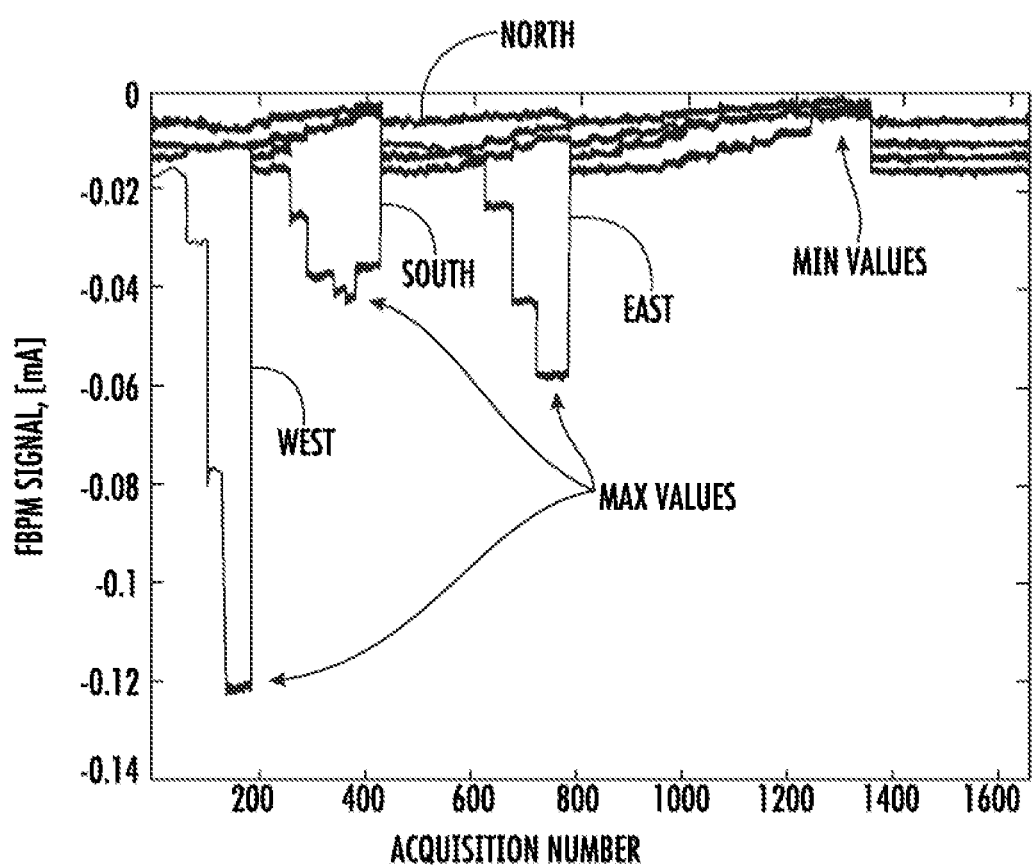
FIG. 4 is a graph image illustrating example waveforms of current collected on electrodes of an example beam position monitor (BPM) during artificial mis-alignment.

In examples, operation of the example BPM 30 was tested on an example low energy beamline (LEBL) (e.g., 190 including pre-accelerator system 20) of an example neutron beam system (NB S) 10. In the tests, a total negative hydrogen ion beam current in the LEBL was approximately 12 milliamps (mA). To demonstrate performance of the BPM 30, the beam was intentionally deviated from the beamline axis using X- and Y-steering magnets. The current waveforms collected by each BPM electrode 36 are shown in FIG. 4. Shown in FIG. 4, the BPM electrodes 36 collect larger currents when the beam is intentionally mis-aligned using the X- and Y-steering magnets. The maximum current values are displayed as well as minimum current values. Based on the results illustrated in FIG. 4, the threshold current for each FBPM electrode 36 may be defined to signal to the control system that the beam is misaligned. The response time of the BPM 30 was 4 microseconds (µs) in the tests used for generation of the results depicted in FIG. 4.

The small magnitude of the beam current collected by the BPM electrodes 36 during normal operation advantageously ensures a long life time of the BPM 30. That is, due to the small magnitude of the beam current collected by the BPM electrodes 36, beam induced damage resulting in expiration of one or more components of the BPM 30 may be avoided or significantly delayed.

The example BPM advantageously enables detection of abnormal beam behavior with microsecond resolution. In certain embodiments, a response time of the BPM may be based on acquisition rates of the reading electronics. The BPM advantageously provides a rapid alarming/notification of beam misalignment to a control system.

The BPM 30 advantageously allows independent adjustment of the insertion length of each electrode 36 (e.g., an extension distance of the electrode into an interior of the beamline) so that small beam deviations can be detected faster (e.g., with a reduced response time) with larger signals. This improves the BPM's reaction time for beams of arbitrary (including rather complex) shape.

Each electrode 36 may be associated with a unique electrode position within the beam position monitor (BPM), and each unique electrode position may be adjustable. Accordingly, while a pair of electrodes may be separated by a given distance, such distance is also adjustable.

BPM 30 is not limited to use in the specific examples described herein, and can also be used in beam systems implemented in industrial or manufacturing processes, such as the manufacturing of semiconductor chips, the alteration of material properties (such as surface treatment), the irradiation of food, and pathogen destruction in medical sterilization. BPM 30 can further be used in imaging applications, such as cargo or container inspection. And by way of another non-exhaustive example, BPM 30 can be used in particle accelerators for medical applications, such as medical diagnostic systems, medical imaging systems, or other non-BNCT radiation therapy systems.

Figure 5:
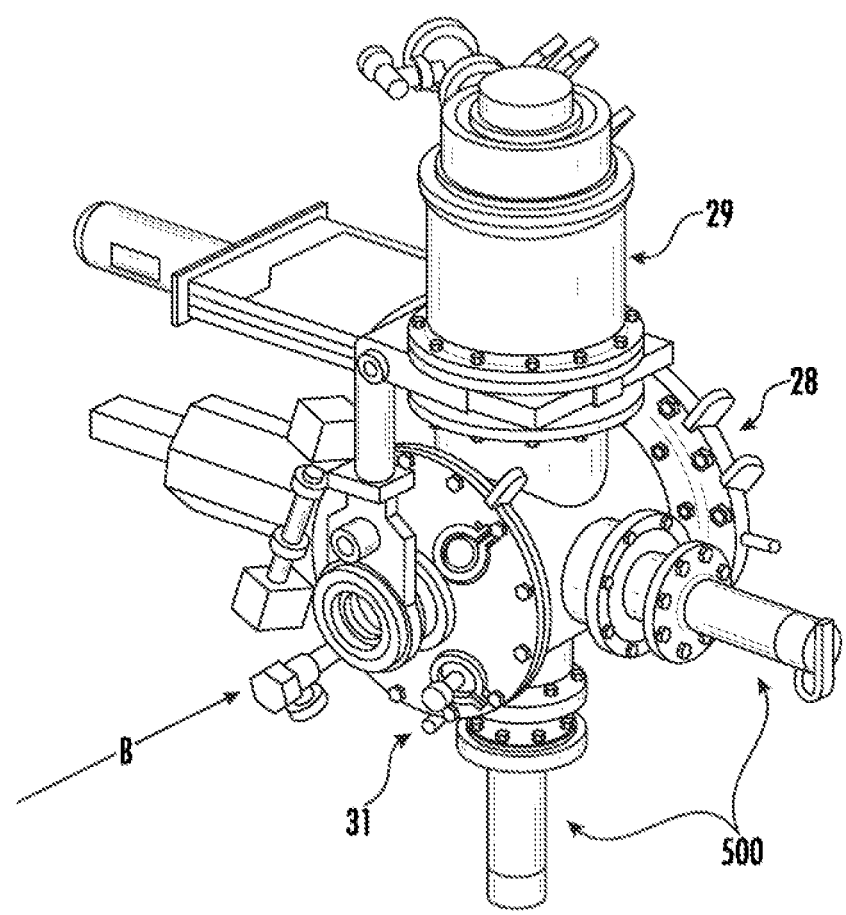
FIG. 5 is a perspective view of an embodiment of the pumping chamber of the ion beam injector system shown in FIG. 2 with a beam imaging (e.g., GPBI) diagnostics system.

Turning to FIG. 5, a pumping chamber 28 may have multiple sets (e.g., two, as depicted in FIG. 5) of beam imaging diagnostics 500 installed in transverse (e.g., orthogonal) directions to a beam propagation axis B. Such an arrangement of beam imaging diagnostics 500 enables characterization of the beam in a direction transverse to that of beam propagation. A gas puff port 31 (partially shown) extends from the pumping chamber 28 and provides a passage into the interior of the pumping chamber 28. A turbomolecular pump 29 on the top of the pumping chamber 28 may be used to pump out gas puffed in through the gas puff port 31. The turbomolecular pump 29 may also maintain a desired or required background gas pressure in the low energy beam line 20.

Figure 6:
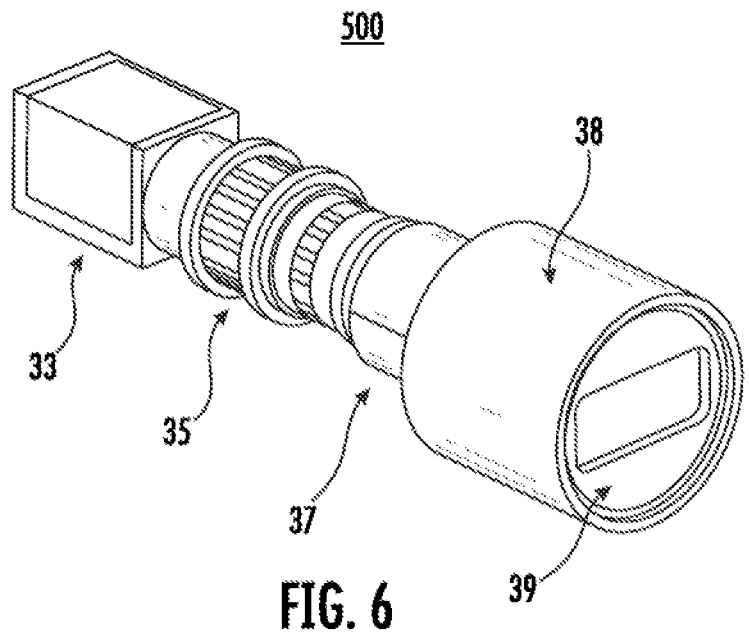
FIG. 6 is a perspective view of an imaging component of the beam imaging (GPBI) diagnostics system for a pulsed beam.

FIG. 6 illustrates an example embodiment of a beam imaging diagnostics system 500. In embodiments, a recording device or imaging component 33 (e.g., camera) may be coupled with a lens 35. The lens 35 may be used to determine a field of view and spatial resolution of the beam imaging diagnostics system 500. An aperture 39 at the end of an optical tube 38 may be matched or aligned with the recording device (e.g., camera) 33 and lens 35 and used to cut off most of a background light which otherwise may reach a sensor (not shown) of the recording device or imaging component (e.g., camera). To further reduce the background noise (e.g., background light), an interference bandpass filter (not shown) can optionally be installed inside a filter holder 37, which may be positioned between the optical tube 38 and lens 35.

A gas puff may be driven by a gas valve (not shown), coupled to the gas puff valve 31 (shown in FIG. 5). The gas valve (not shown) may drive the gas puff with a controlled duration of the gas valve open state enabling control of an amount of gas puffed into the pumping chamber 28 as well as control or selection of a time when the gas is puffed into the pumping chamber 28.

Figure 11A:
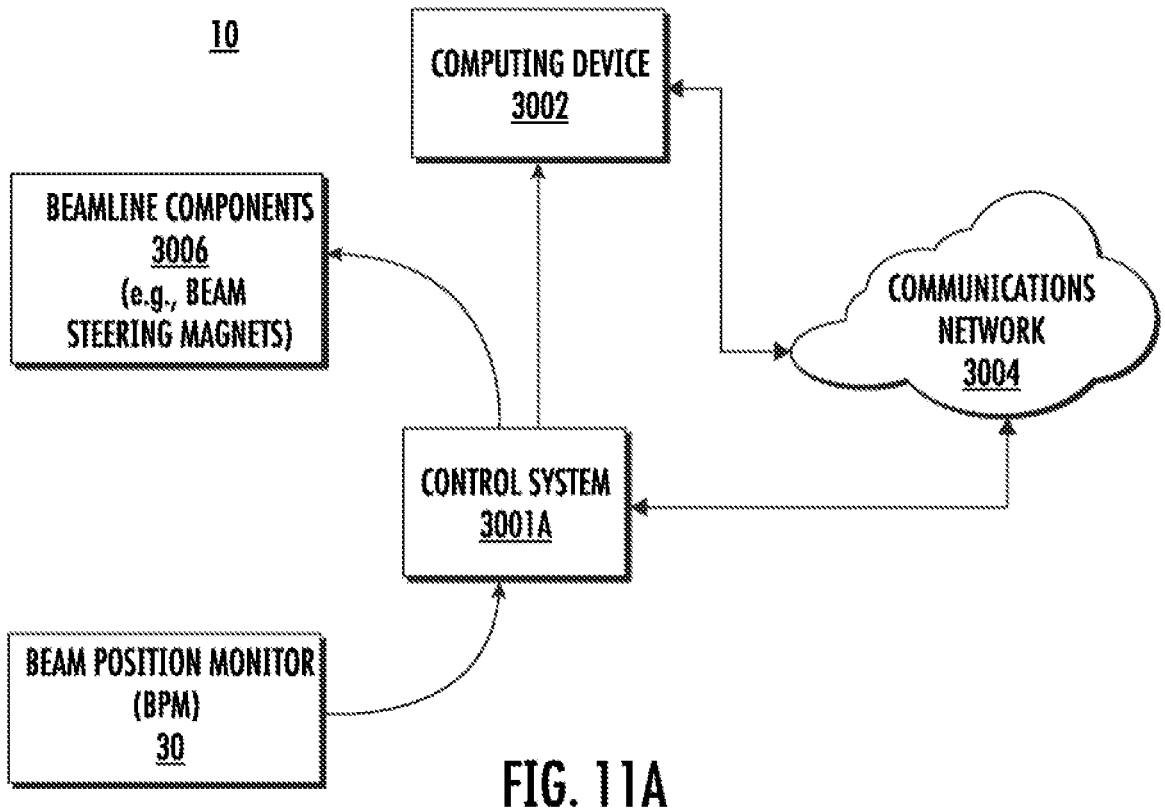
FIGS. 11A and 11B illustrate block diagrams depicting example embodiments of a control system with which embodiments of the present disclosure may operate.
Figure 11B:
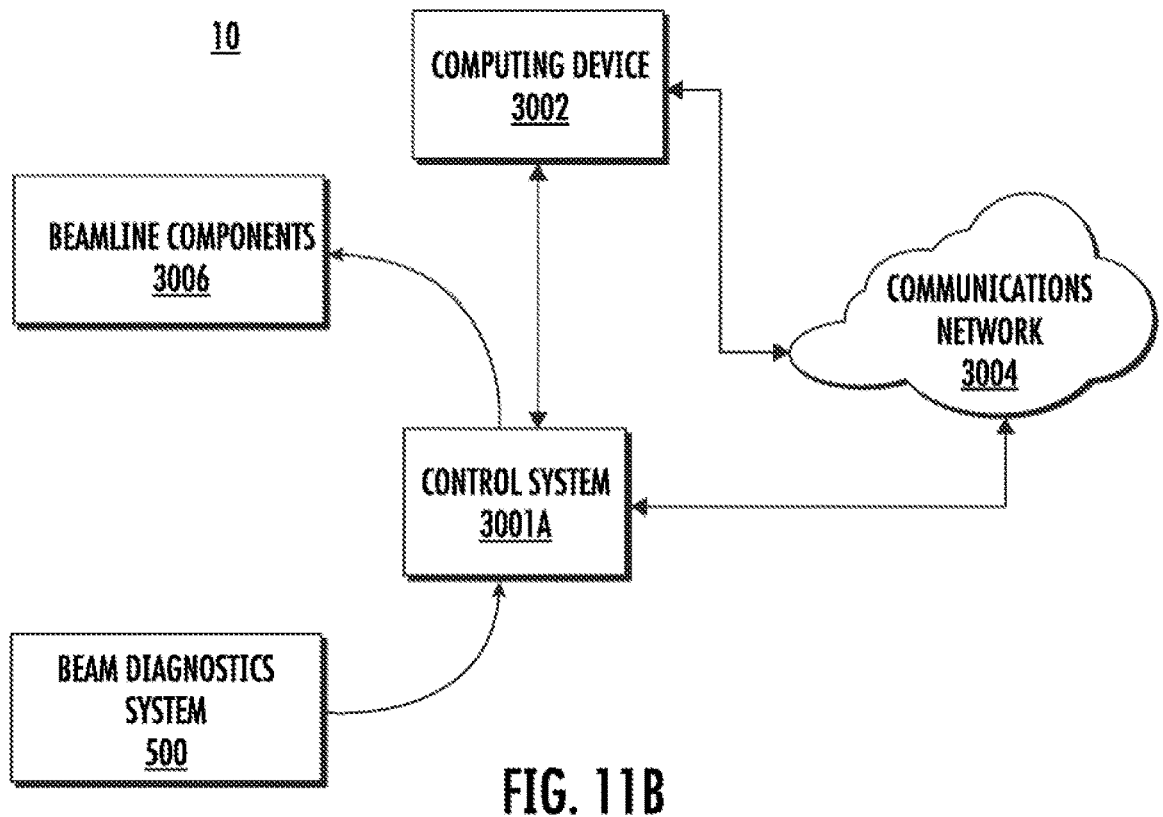

The gas valve, recording device(s) and other components of the beam imaging diagnostics system 500 may be controlled by way of a control system (not shown; an example of which is depicted in FIGS. 11A and 11B).

It may be desirable to select a location of the gas puffing and the nozzle structure in order to achieve uniform distribution of the gas within the field of view of the recording device or imaging component 33 (e.g., camera). This can significantly improve the linearity of the collected signal and simplify the data analysis.

Figure 7:
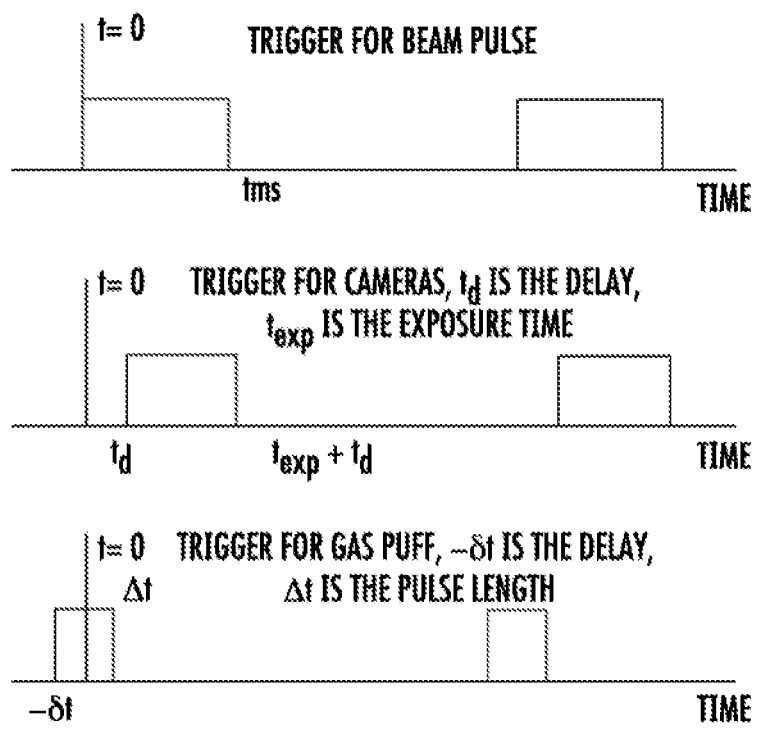
FIG. 7 illustrates an example timing scheme for use with embodiments of the present disclosure.

In example embodiments, an example beam imaging diagnostic system 500 may be configured to track a charged particle beam of a beam system operating in both DC and pulsed modes. This may be implemented according to an example timing scheme shown in FIG. 7. The triggering of the beam imaging diagnostic system 500 may be arbitrary for DC beams. In the case of pulsed beam generation, the gas valve may be triggered prior to the beam pulse in order to ensure presence of the gas within the diagnostic field of view of the beam diagnostics system 500, as well as uniformity of the gas. The recording device or imaging component (e.g., camera) trigger may be delayed relative to the beam pulse in order to accommodate for beam equilibration time as well as fluorescent emission delay. A camera detector exposure time may be adjusted to accumulate as much of the signal as possible while keeping the signal-to-noise (SNR) ratio at the highest level.

Figure 8:
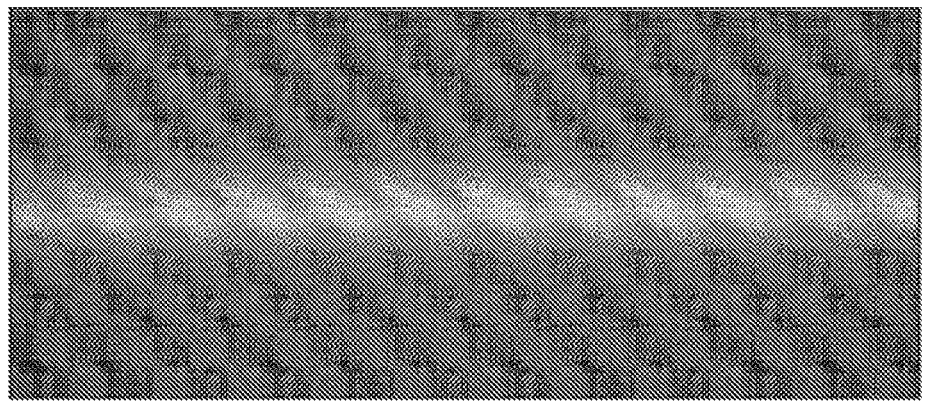
FIG. 8 is an example beam image acquired by the gas puff beam imaging (GPBI) diagnostic system.

A raw image acquired by an example recording device (e.g., camera) of an example beam imaging diagnostics system 500 is shown in FIG. 8. The beam visible in the middle of the image. That is, 30 keV, 12 mA of negative hydrogen ions is propagating from the left to right in the image of FIG. 8. The uniform black background is formed by a viewing dump (not shown) installed inside the vacuum chamber. The post-processed image with background subtracted, artificially rescaled to emphasize the beam and showing about 10 millimeter (mm) beam length is presented in FIG. 9.

Figure 9:
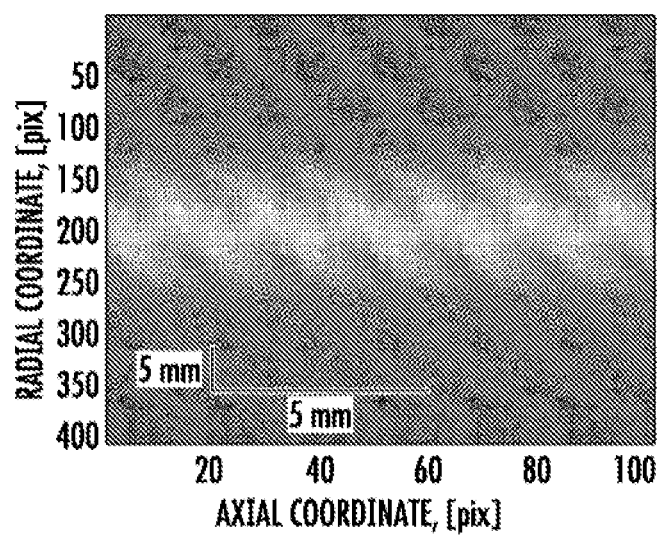
FIG. 9 is an example of a post-processed image shown in FIG. 8.

The image in FIG. 9, cleared from the background light, may be further used to obtain the beam position inside the LEBL, transverse size, and beam inclination which in real-time are transferred to a control system (see, e.g., FIGS.

11A, 11B). The beam size is estimated at 90% of the beam current. This level can be adjusted depending on either assumed or measured beam current distribution. The image SNR can be further improved by using the bandpass filter (see, e.g., FIG. 6) to restrict collection to useful signal and enable more effective cutting off of the background light.

Figure 10:
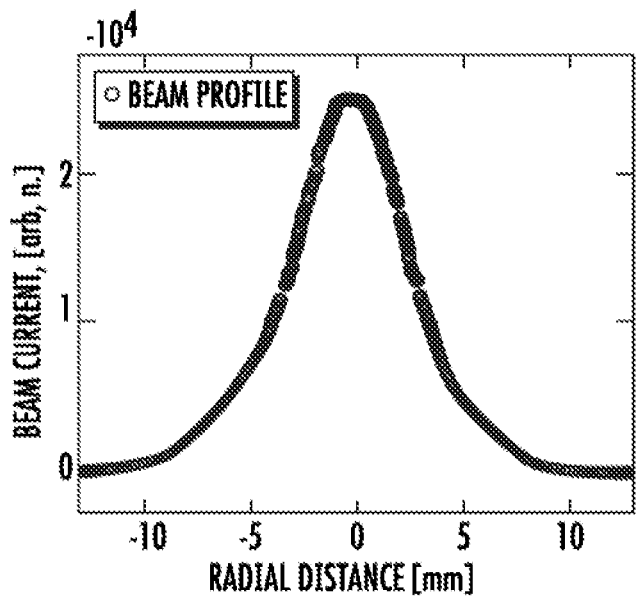
FIG. 10 is a graph showing an example of the measured beam line-integrated profile.

An example of the measured beam line-integrated profile is shown in FIG. 10, which illustrates the Gaussian like beam current distribution and shows that the beam size is about 10 mm calculated at 90% level of the beam current. The radial distance in FIG. 10 is zeroed at the beam centroid (compare with FIG. 9). The actual beam profile can be reconstructed from FIG. 10 using, for example, the Abel inversion algorithm (based on a symmetry of the beam), or using tomographic techniques.

To estimate the beam inclination relative to an axis of the low energy beam line (LEBL), the beam centroids are calculated along the beam propagation and compared with beamline axis coordinates obtained during calibration of the beam imaging diagnostic system.

Beam imaging diagnostics system 500 can be placed in any desired location of the beamline, either on the lower energy side of the accelerator, in the accelerator itself, or on the higher energy side. System 500 is not limited to use in the specific examples described herein, and can also be used in beam systems implemented in industrial or manufacturing processes, such as the manufacturing of semiconductor chips, the alteration of material properties (such as surface treatment), the irradiation of food, and pathogen destruction in medical sterilization. System 500 can further be used in imaging applications, such as cargo or container inspection. And by way of another non-exhaustive example, system 500 can be used in particle accelerators for medical applications, such as medical diagnostic systems, medical imaging systems, or other non-BNCT radiation therapy systems.

FIGS. 11A and 11B are block diagrams depicting example embodiments of a control system with which embodiments of the present disclosure may operate. For example, the illustrated example system includes beam system 10 and one or more computing devices 3002. In embodiments, beam system 10 may be part of an example neutron beam system (e.g., system 10 above). In such embodiments, the beam system 10 may employ one or more control systems 3001A with which one or more computing devices 3002 may communicate in order to interact with the systems and components of the beam system 10 (e.g., neutron beam system 10). Each of these devices and/or systems are configured to communicate directly with one another or via a local network, such as network 3004.

Computing devices 3002 may be embodied by various user devices, systems, computing apparatuses, and the like. For example, a first computing device 3002 may be a desktop computer associated with a particular user, while another computing device 3002 may be a laptop computer associated with a particular user, and yet another computing device 3002 may be a mobile device (e.g., a tablet or smart device). Each of the computing devices 3002 may be configured to communicate with the beam system 10, for example through a user interface accessible via the computing device. For example, a user may execute a desktop application on the computing device 3002, which is configured to communicate with the beam system 10.

By using a computing device 3002 to communicate with beam system 10, a user may provide operating parameters for the beam system 10 (e.g., operating voltages, and the like) according to embodiments described herein. In embodiments, beam system 10 may include a control system 3001A by which beam system 10 may receive and apply operating parameters from computing device 3002.

Control system 3001A may be configured to receive measurements, signals, or other data from components of the beam system 10. For example, control system 3001A may receive signals from an example beam position monitor (BPM) 30 (e.g., FIG. 11A) indicative of a position of a beam passing through the beam system 10. The control system 3001A, depending on the position of the beam passing through the beam system, may provide adjustments to inputs of one or more beam line components 3006, such as beam steering magnets, to alter the position of the beam according to the methods described herein. The control system 3001A may also provide information collected from any of the components of the beam system 10, including the beam position monitor (BPM) 30 (e.g., FIG. 11A), to the computing device 3002 either directly or via communications network 3004.

For example, control system 3001A may receive signals from an example beam diagnostics system 500 (e.g., FIG. 11B) indicative of a beam position of a beam passing through the beam system 10, a transverse size of the beam, a beam inclination of the beam, beam current distribution, and the like. The control system 3001A, depending on the received signals, may provide adjustments to inputs of one or more beam line components 3006, to alter the position or other parameters of the beam according to the methods described herein. For example, the control system 3001A may trigger a gas valve prior to a beam pulse in order to ensure presence of the gas within the diagnostic field of view of a beam diagnostics system 500 (e.g., FIG. 11B), as well as uniformity of the gas. The control system 3001A may further delay a trigger of a recording device or imaging component (e.g., camera) relative to the beam pulse in order to accommodate for beam equilibration time as well as fluorescent emission delay. The control system 3001A may further adjust a camera detector exposure time to accumulate as much of the signal as possible while keeping the signal-to-noise (SNR) ratio at the highest level.

The control system 3001A may also provide information collected from any of the components of the beam system 10, including the beam diagnostics system 500 (e.g., FIG. 11B), to the computing device 3002 either directly or via communications network 3004.

Communications network 3004 may include any wired or wireless communication network including, for example, a wired or wireless local area network (LAN), personal area network (PAN), metropolitan area network (MAN), wide area network (WAN), or the like, as well as any hardware, software and/or firmware required to implement it (such as, e.g., network routers, etc.). For example, communications network 3004 may include an 802.11, 802.16, 802.20, and/or WiMax network. Further, the communications network 3004 may include a public network, such as the Internet, a private network, such as an intranet, or combinations thereof, and may utilize a variety of networking protocols now available or later developed including, but not limited to TCP/IP based networking protocols.

Figure 12:
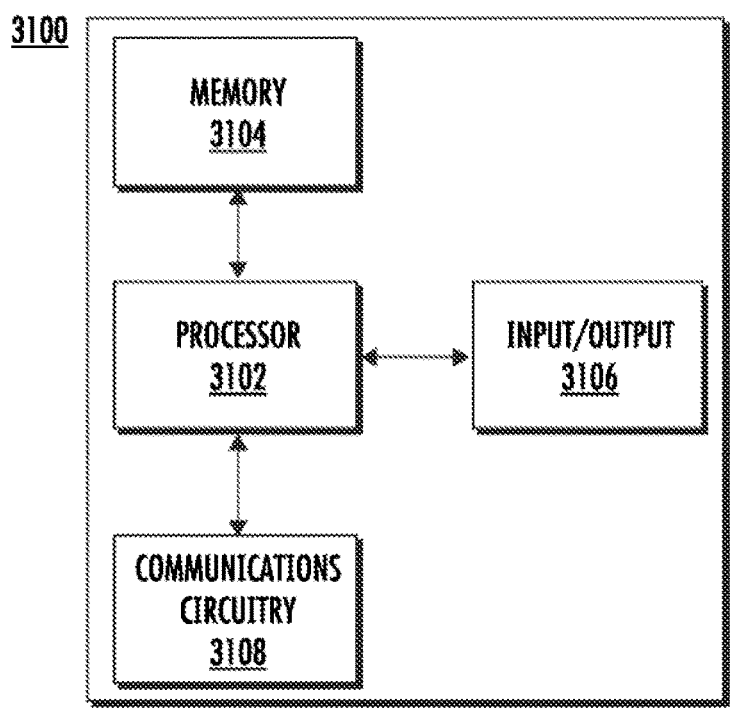
FIG. 12 is a block diagram depicting an example embodiment of a computing apparatus that may be used with embodiments of the present disclosure.

The computing device 3002 and control system 3001A may be embodied by one or more computing systems, such as apparatus 3100 shown in FIG. 12. As illustrated in FIG. 12, the apparatus 3100 may include a processor 3102, a memory 3104, an input and/or output circuitry 3106, and communications device or circuitry 3108. It should also be understood that certain of these components 3102-3108 may include similar hardware. For example, two components may both leverage use of the same processor, network interface, storage medium, or the like to perform their associated functions, such that duplicate hardware is not required for each device. The use of the terms "device" and/or "circuitry" as used herein with respect to components of the apparatus therefore can encompass particular hardware configured with software to perform the functions associated with that particular device, as described herein.

The terms "device" and/or "circuitry" should be understood broadly to include hardware, in some embodiments, device and/or circuitry may also include software for configuring the hardware. For example, in some embodiments, device and/or circuitry may include processing circuitry, storage media, network interfaces, input/output devices, and the like. In some embodiments, other elements of the apparatus 3100 may provide or supplement the functionality of particular device(s). For example, the processor 3102 may provide processing functionality, the memory 3104 may provide storage functionality, the communications device or circuitry 3108 may provide network interface functionality, and the like.

In some embodiments, the processor 3102 (and/or co-processor or any other processing circuitry assisting or otherwise associated with the processor) may be in communication with the memory 3104 via a bus for passing information among components of the apparatus. The memory 3104 may be non-transitory and may include, for example, one or more volatile and/or non-volatile memories. In other words, for example, the memory may be an electronic storage device (e.g., a computer readable storage medium.) The memory 3104 may be configured to store information, data, content, applications, instructions, or the like, for enabling the apparatus to carry out various functions in accordance with example embodiments of the present disclosure.

The processor 3102 may be embodied in a number of different ways and may, for example, include one or more processing devices configured to perform independently. Additionally or alternatively, the processor may include one or more processors configured in tandem via a bus to enable independent execution of instructions, pipelining, and/or multithreading. The use of the terms "processing device" and/or "processing circuitry" may be understood to include a single core processor, a multi-core processor, multiple processors internal to the apparatus, and/or remote or "cloud" processors.

In an example embodiment, the processor 3102 may be configured to execute instructions stored in the memory 3104 or otherwise accessible to the processor. Alternatively or additionally, the processor may be configured to execute hard-coded functionality. As such, whether configured by hardware or software methods, or by a combination of hardware with software, the processor may represent an entity (e.g., physically embodied in circuitry) capable of performing operations according to an embodiment of the present disclosure while configured accordingly. Alternatively, as another example, when the processor is embodied as an executor of software instructions, the instructions may specifically configure the processor to perform the algorithms and/or operations described herein when the instructions are executed.

In some embodiments, the apparatus 3100 may include input/output device 3106 that may, in turn, be in communication with processor 3102 to provide output to the user and, in some embodiments, to receive input from the user. The input/output device 3106 may include a user interface and may include a device display, such as a user device display, that may include a web user interface, a mobile application, a client device, or the like. In some embodiments, the input/output device 3106 may also include a keyboard, a mouse, a joystick, a touch screen, touch areas, soft keys, a microphone, a speaker, or other input/output mechanisms. The processor and/or user interface circuitry including the processor may be configured to control one or more functions of one or more user interface elements through computer program instructions (e.g., software and/or firmware) stored on a memory accessible to the processor (e.g., memory 3104, and/or the like).

The communications device or circuitry 3108 may be any means such as a device or circuitry embodied in either hardware or a combination of hardware and software that is configured to receive and/or transmit data from/to a network and/or any other device or circuitry in communication with the apparatus 3100. In this regard, the communications device or circuitry 3108 may include, for example, a network interface for enabling communications with a wired or wireless communication network. For example, the communications device or circuitry 3108 may include one or more network interface cards, antennas, buses, switches, routers, modems, and supporting hardware and/or software, or any other device suitable for enabling communications via a network. Additionally or alternatively, the communication interface may include the circuitry for interacting with the antenna(s) to cause transmission of signals via the antenna(s) or to handle receipt of signals received via the antenna(s). These signals may be transmitted by the apparatus 3100 using any of a number of wireless personal area network (PAN) technologies, such as current and future Bluetooth standards (including Bluetooth and Bluetooth Low Energy (BLE)), infrared wireless (e.g., IrDA), FREC, ultra-wideband (UWB), induction wireless transmission, or the like. In addition, it should be understood that these signals may be transmitted using Wi-Fi, Near Field Communications (NFC), Worldwide Interoperability for Microwave Access (WiMAX), or other proximity-based communications protocols.

As will be appreciated, any such computer program instructions and/or other type of code may be loaded onto a computer, processor, or other programmable apparatus' circuitry to produce a machine, such that the computer, processor, or other programmable circuitry that executes the code on the machine creates the means for implementing various functions, including those described herein.

As described above and as will be appreciated based on this disclosure, embodiments of the present disclosure may be configured as systems, methods, mobile devices, backend network devices, and the like. Accordingly, embodiments may comprise various means including entirely of hardware or any combination of software and hardware. Furthermore, embodiments may take the form of a computer program product on at least one non-transitory computer-readable storage medium having computer-readable program instructions (e.g., computer software) embodied in the storage medium. Any suitable computer-readable storage medium may be utilized including non-transitory hard disks, CD-ROMs, flash memory, optical storage devices, or magnetic storage devices.

Processing circuitry for use with embodiments of the present disclosure can include one or more processors, microprocessors, controllers, and/or microcontrollers, each of which can be a discrete chip or distributed amongst (and a portion of) a number of different chips. Processing circuitry for use with embodiments of the present disclosure can include a digital signal processor, which can be implemented in hardware and/or software of the processing circuitry for use with embodiments of the present disclosure. Processing circuitry for use with embodiments of the present disclosure can be communicatively coupled with the other components of the figures herein. Processing circuitry for use with embodiments of the present disclosure can execute software instructions stored on memory that cause the processing circuitry to take a host of different actions and control the other components in figures herein.

Memory for use with embodiments of the present disclosure can be shared by one or more of the various functional units, or can be distributed amongst two or more of them (e.g., as separate memories present within different chips). Memory can also be a separate chip of its own. Memory can be non-transitory, and can be volatile (e.g., RAM, etc.) and/or non-volatile memory (e.g., ROM, flash memory, F-RAM, etc.).

Computer program instructions for carrying out operations in accordance with the described subject matter may be written in any combination of one or more programming languages, including an object oriented programming language such as Java, JavaScript, Smalltalk, C++, C#, Transact-SQL, XML, PHP or the like and conventional procedural programming languages, such as the "C" programming language or similar programming languages.

Various aspects of the present subject matter are set forth below, in review of, and/or in supplementation to, the embodiments described thus far, with the emphasis here being on the interrelation and interchangeability of the following embodiments. In other words, an emphasis is on the fact that each feature of the embodiments can be combined with each and every other feature unless explicitly stated otherwise or logically implausible.

In some embodiments, a beam position monitor includes multiple electrodes extending into an interior of a component of a beam line. In some of these embodiments, the beam position monitor is configured to detect a position of a beam passing through the component of the beam line based on halo current of the beam. In some of these embodiments, the beam position monitor further includes a cooling device.

In some of these embodiments, each electrode of the multiple electrodes is associated with a current threshold. In some of these embodiments, at least one electrode of the multiple electrodes is associated with a different current threshold than one or more other electrodes of the multiple electrodes. In some of these embodiments, each electrode of the multiple electrodes is associated with multiple current thresholds.

In some of these embodiments, the beam position monitor is configured to transmit a signal to a control system when a measured current by one or more electrode of the multiple electrodes exceeds its associated current threshold. In some of these embodiments, the beam position monitor is configured to transmit a signal to a control system when a measured current by adjacent electrodes of the multiple electrodes exceeds a lower threshold of the multiple current thresholds associated with each electrode of the adjacent electrodes.

In some of these embodiments, each electrode of the multiple electrodes is associated with an electrode extension distance. In some of these embodiments, the electrode extension distance represents a distance into the interior of the component that the electrode extends. In some of these embodiments, each electrode extension distance is adjustable.

In some of these embodiments, the multiple electrodes are galvanically isolated from a wall of the beam position monitor. In some of these embodiments, the multiple electrodes are configured to be biased by an external power supply.

In some of these embodiments, the beam position monitor is configured to transmit a signal to a control system when a beam advancing through the beam line is off axis. In some of these embodiments, a minimal amount of a beam current of the beam passing through the component of the beam line is reduced due to the multiple electrodes.

In some embodiments, a beam system includes a beam position monitor configured to detect a position of a beam passing through a component of a beam line based on halo current of the beam. In some of these embodiments, the beam system further includes a control system configured to adjust beam line parameters based on the position of the beam.

In some of these embodiments, the beam position monitor includes multiple electrodes extending into an interior of the component of the beam line.

In some of these embodiments, the control system includes at least one processor and at least one memory storing instructions that, when executed by the at least one processor, cause the control system to receive one or more signals from the beam position monitor and, based on the one or more signals, transmit instructions to discontinue operation of the beam system.

In some of these embodiments, the control system includes at least one processor and at least one memory storing instructions that, when executed by the at least one processor, cause the control system to receive one or more signals from the beam position monitor and, based on the one or more signals, transmit data representative of the one or more signals to a computing device.

In some of these embodiments, the control system includes at least one processor and at least one memory storing instructions that, when executed by the at least one processor, cause the control system to receive one or more signals from the beam position monitor. In some of these embodiments, the control system is caused to, based on the one or more signals, determine that the beam is off a desired axis, and transmit adjustment signals to one or more beam line components to adjust the position of the beam such that it returns to the desired axis.

In some of these embodiments, the control system includes at least one processor and at least one memory storing instructions that, when executed by the at least one processor, cause the control system to receive one or more signals from the beam position monitor. In some of these embodiments, the control system is further caused to, based on the one or more signals, determine a degree of beam deflection off a desired axis, and transmit adjustment signals to one or more beam line components to compensate for the degree of beam deflection off the desired axis.

In some of these embodiments, the one or more beam line components include one or more beam steering magnets. In some of these embodiments, the adjustment signals adjust positions of the one or more beam steering magnets.

In some of these embodiments, the one or more signals represent measured current by one or more electrodes of the multiple electrodes.

In some of these embodiments, the one or more signals represent measured current by one or more electrodes of the multiple electrodes exceeding a current threshold associated with the one or more electrodes.

In some of these embodiments, the one or more signals represent measured current by adjacent electrodes of the multiple electrodes exceeding a current threshold associated with the adjacent electrodes.

In some of these embodiments, the beam system includes a beam position monitor according to any of the foregoing embodiments.

In some of these embodiments, the beam system includes an ion source configured to generate ions and a tandem accelerator configured to accelerate ions propagated from the ion source. In some of these embodiments, one or more beam position monitors are positioned one or more of upstream the tandem accelerator or downstream the tandem accelerator.

In some embodiments, a neutron beam system includes a pre-accelerator system configured to accelerate ions from an ion source, a tandem accelerator configured to accelerate ions from the pre-accelerator system, and a beam position monitor according to any of the foregoing embodiments. In some of these embodiments, the ion source is configured to generate ions.

In some of these embodiments, the neutron beam system further includes a beamline coupled to an outlet of the tandem accelerator, and the pre-accelerator system coupled to an inlet of the tandem accelerator.

In some of these embodiments, the pre-accelerator system includes one or more of an einzel lens, a pre-accelerator tube, a magnetic focusing elements, or a pumping chamber.

In some embodiments, a method of monitoring a position of a beam advancing through a beam line includes measuring a magnitude of a current at one or more individual electrodes of multiple electrodes positioned within a beam line as a beam advances through the beam line. In some of these embodiments, each individual electrode of the multiple electrodes is associated with one or more current thresholds.

In some of these embodiments, the method further includes determining whether the beam advancing through the beam line is off axis by comparing the magnitude of the current at one or more of the one or more individual electrodes against one or more current thresholds.

In some of these embodiments, the method further includes determining whether the beam advancing through the beam line is off axis by comparing a first magnitude of current at a first electrode of the one or more individual electrodes to a first current threshold and a second magnitude of current at a second electrode of the one or more individual electrodes to a second current threshold. In some of these embodiments, the first electrode and the second electrode are positioned adjacent one another.

In some of these embodiments, the method further includes signaling to a control system that the beam is off axis when the magnitude of the current at one or more of the one or more individual electrodes exceeds or is below the one or more current thresholds.

In some of these embodiments, the method further includes signaling to a control system that the beam is off axis when the first magnitude of current at the first electrode exceeds or is below the first current threshold and the second magnitude of current at the second electrode exceeds or is below the second current threshold.

In some of these embodiments, the method further includes biasing the multiple electrodes using an external power supply. In some of these embodiments, the method further includes water cooling the multiple electrodes.

In some of these embodiments, each individual electrode of the plurality of electrodes is associated with an electrode extension distance. In some of these embodiments, an electrode extension distance represents a distance into the interior of a component of the beam line that an electrode extends.

In some of these embodiments, each individual electrode is associated with a unique predetermined threshold current.

In some embodiments, a method of controlling a position of a beam advancing through a beam line of a beam system includes receiving, from a beam position monitor, one or more signals, and determining, based on the one or more signals, whether the beam advancing through the beam line is off axis.

In some of these embodiments, the beam position monitor includes multiple electrodes extending into an interior of a component of the beam line.

In some of these embodiments, the method further includes, based on the one or more signals, transmitting instructions to discontinue operation of the beam system. In some of these embodiments, the method further includes, based on the one or more signals, transmitting data representative of the one or more signals to a computing device.

In some of these embodiments, the method further includes, upon determining that the beam is off a desired axis, transmitting adjustment signals to one or more beam line components to adjust the position of the beam such that it returns to the desired axis.

In some of these embodiments, the method further includes, based on the one or more signals, determining a degree of beam deflection off a desired axis and transmitting adjustment signals to one or more beam line components to compensate for the degree of beam deflection off the desired axis.

In some of these embodiments, the one or more beam line components comprise one or more beam steering magnets. In some of these embodiments, the adjustment signals adjust positions of the one or more beam steering magnets.

In some of these embodiments, the one or more signals represent measured current by one or more electrodes of the multiple electrodes. In some of these embodiments, the one or more signals represent measured current by one or more electrodes of the multiple electrodes exceeding a current threshold associated with the one or more electrodes. In some of these embodiments, the one or more signals represent measured current by adjacent electrodes of the multiple electrodes exceeding a current threshold associated with the adjacent electrodes.

In some of these embodiments, the degree of beam deflection quantifies how far off axis the beam is traveling.

In some embodiments, a beam imaging diagnostics system includes two (2) or more imaging components coupled to and extending into an interior of a pumping chamber and orthogonally oriented to a beam propagation axis of the pumping chamber. In some of these embodiments, the pumping chamber is positionable along a beam line. In some of these embodiments, the two (2) or more imaging components are configured to substantially non-invasively monitor a beam advancing through the beam line with the injection of a gas. In some of these embodiments, the beam imaging diagnostics system is configured to monitor beam parameters of the beam advancing through the beam line. In some of these embodiments, beam parameters comprise one or more of size, location, inclination, or profile.

In some of these embodiments, the beam imaging diagnostics system further includes a gas puff port extending from the pumping chamber and providing a passage into the pumping chamber. In some of these embodiments, the two (2) or more imaging components include a camera coupled with a lens. In some of these embodiments, an optical tube is one or more of indirectly or directly coupled with the lens. In some of these embodiments, an end of the optical tube that is farthest from the camera includes an aperture having an opening of a specific shape. In some of these embodiments, the aperture is matched with the camera and configured to cut off most of a background light which otherwise may reach a camera sensor of the camera. In some of these embodiments, the two (2) or more imaging components further include an interference bandpass filter positioned between the optical tube and the lens.

In some of these embodiments, the gas puff port is driven by a gas valve.

In some of these embodiments, the two (2) or more imaging components include an adjustable detector exposure time. In some of these embodiments, the adjustable detector exposure time is adjustable to provide for accumulation of as much of a signal as possible while maintaining a highest possible signal-to-noise ratio (SNR).

In some of these embodiments, the gas valve is configured to control an amount of gas puffed and a time when the amount of gas is puffed into the pumping chamber. In some of these embodiments, the gas valve is further configured to control a location of gas puffed into the pumping chamber such that a uniform distribution of gas is achieved within a field of view of the two (2) or more imaging components.

In some of these embodiments, the camera includes one or more of a time resolution, a signal-to-noise ratio, or a size. In some of these embodiments, the time resolution is 2 milliseconds or less. In some of these embodiments, the signal-to-noise ratio exceeds 40:1.

In some embodiments, a beam system includes a beam imaging diagnostics system positioned along the beam system. In some of these embodiments, the beam imaging diagnostics system is configured to non-invasively monitor a beam advancing through the beam system. In some of these embodiments, the beam system further includes a control system configured to receive one or more signals from the beam imaging diagnostics system.

In some of these embodiments, the beam imaging diagnostics system includes a beam imaging diagnostics system according to any of the foregoing embodiments.

In some of these embodiments, the control system includes at least one processor and at least one memory storing instructions that, when executed by the at least one processor, cause the control system to, based on the one or more signals, determine one or more beam parameters comprising one or more of size, location, inclination, or profile.

In some of these embodiments, the control system includes at least one processor and at least one memory storing instructions that, when executed by the at least one processor, cause the control system to, based on the one or more signals, transmit a control signal to one or more of a gas valve or one or more imaging components of the beam imaging diagnostics system.

In some of these embodiments, the beam system further includes a low-energy beamline (LEBL). In some of these embodiments, the LEBL includes one or more of a negative ion source, beam optics, a pre-accelerator system, beam diagnostics, or a pumping chamber. In some of these embodiments, the beam system further includes an accelerator downstream the LEBL. In some of these embodiments, a first beam imaging diagnostics system according to any of the foregoing embodiments is positioned upstream the accelerator. In some of these embodiments, a second beam imaging diagnostics system according to any of the foregoing embodiments is positioned downstream the accelerator.

In some embodiments, a neutron beam system includes a pre-accelerator system configured to accelerate ions from an ion source, a tandem accelerator configured to accelerate ions from the pre-accelerator system, and a beam imaging diagnostics system according to any of the foregoing embodiments.

In some of these embodiments, the neutron beam system further includes an ion source configured to generate ions. In some of these embodiments, the neutron beam system further includes a high-energy beamline (HEBL) coupled to an outlet of the tandem accelerator, and the pre-accelerator system coupled to an inlet of the tandem accelerator. In some of these embodiments, the pre-accelerator system includes one or more of an einzel lens, a pre-accelerator tube, a magnetic focusing elements, or a pumping chamber.

In some of these embodiments, the neutron beam system further includes a control system configured to receive one or more signals from the beam imaging diagnostics system.

In some of these embodiments, the control system includes at least one processor and at least one memory storing instructions that, when executed by the at least one processor, cause the control system to, based on the one or more signals, determine one or more beam parameters comprising one or more of size, location, inclination, or profile.

In some of these embodiments, the control system includes at least one processor and at least one memory storing instructions that, when executed by the at least one processor, cause the control system to, based on the one or more signals, transmit a control signal to one or more of a gas valve or one or more imaging components of the beam imaging diagnostics system.

In some embodiments, a method of noninvasively monitoring parameters of a beam advancing along a beam line includes puffing gas into a pumping chamber and measuring one or more beam parameters based on fluorescence resulting from collisions of energetic beam particulates of a beam advancing through the beam line.

In some of these embodiments, the method further includes puffing the gas into the pumping chamber while the beam advances through the beam line.

In some of these embodiments, the method further includes puffing the gas into the pumping chamber along the beam line such that disturbance to the beam advancing through the beam line is minimized.

In some of these embodiments, the method further includes measuring the one or more beam parameters such that disturbance to the beam advancing through the beam line is minimized.

In some of these embodiments, the method further includes puffing the gas into the pumping chamber prior to a pulse of the beam advancing through the beam line.

In some of these embodiments, the one or more beam parameters include one or more of a transverse beam size (profile) or a beam position.

In some of these embodiments, measuring includes recording a glow of fluorescence from a beam-gas interaction region. In some of these embodiments, recording the glow of fluorescence includes recording using two or more orthogonally oriented imaging components. In some of these embodiments, the method further includes delaying a trigger for the two or more orthogonally oriented imaging components relative to a pulse of the beam. In some of these embodiments, the trigger is delayed to accommodate for one or more of beam equilibration time or fluorescent emission delay.

In some of these embodiments, the method further includes transferring one or more beam parameters to a control system. In some of these embodiments, the one or more beam parameters include beam position, transverse size, and beam inclination. In some of these embodiments, the method further includes transferring the one or more beam parameters to the control system in real-time.

In some of these embodiments, the method further includes calculating beam centroids along a beam propagation, and comparing the beam centroids with beamline axis coordinates. In some of these embodiments, the method further includes obtaining the beamline axis coordinates during calibration of a beam imaging diagnostics system.

In some of these embodiments, the method further includes measuring the one or more beam parameters one or more of before treatment, during treatment, or after treatment.

In some of these embodiments, the gas includes one or more of argon or xenon.

It should be noted that all features, elements, components, functions, and steps described with respect to any embodiment provided herein are intended to be freely combinable and substitutable with those from any other embodiment. If a certain feature, element, component, function, or step is described with respect to only one embodiment, then it should be understood that that feature, element, component, function, or step can be used with every other embodiment described herein unless explicitly stated otherwise. This paragraph therefore serves as antecedent basis and written support for the introduction of claims, at any time, that combine features, elements, components, functions, and steps from different embodiments, or that substitute features, elements, components, functions, and steps from one embodiment with those of another, even if the following description does not explicitly state, in a particular instance, that such combinations or substitutions are possible. It is explicitly acknowledged that express recitation of every possible combination and substitution is overly burdensome, especially given that the permissibility of each and every such combination and substitution will be readily recognized by those of ordinary skill in the art.

To the extent the embodiments disclosed herein include or operate in association with memory, storage, and/or computer readable media, then that memory, storage, and/or computer readable media are non-transitory. Accordingly, to the extent that memory, storage, and/or computer readable media are covered by one or more claims, then that memory, storage, and/or computer readable media is only non-transitory.

As used herein and in the appended claims, the singular forms "a," "an," and "the" include plural referents unless the context clearly dictates otherwise.

While the embodiments are susceptible to various modifications and alternative forms, specific examples thereof have been shown in the drawings and are herein described in detail. It should be understood, however, that these embodiments are not to be limited to the particular form disclosed, but to the contrary, these embodiments are to cover all modifications, equivalents, and alternatives falling within the spirit of the disclosure. Furthermore, any features, functions, steps, or elements of the embodiments may be recited in or added to the claims, as well as negative limitations that define the inventive scope of the claims by features, functions, steps, or elements that are not within that scope.

What is claimed is:

1. A beam position monitor positioned along a beam system configured for boron neutron capture therapy, the beam system comprising an ion source, an accelerator, and a target, the beam position monitor comprising a plurality of electrodes extending into an interior of a component of a beam line of the beam system, wherein the beam position monitor is configured to detect a position of a beam passing through the component of the beam line based on halo current of the beam, wherein each electrode of the plurality of electrodes is configured to collect current measurements based on exposure of the electrode to the halo current of the beam, wherein each electrode of the plurality of electrodes has an elongate shape and a long axis, wherein the long axis extends into the interior of the component in a direction perpendicular to a wall of the beam position monitor at a position where the electrode is coupled with the wall, and wherein the beam position monitor is positioned between the accelerator and the target.

2. The beam position monitor of claim 1, further comprising a cooling device.

3. The beam position monitor of claim 1, wherein each electrode of the plurality of electrodes is associated with a current threshold.

4. The beam position monitor of claim 3, wherein the beam position monitor is configured to transmit a signal to a control system when a measured current by one or more electrode of the plurality of electrodes exceeds its associated current threshold.

5. The beam position monitor of claim 1, wherein at least one electrode of the plurality of electrodes is associated with a different current threshold than one or more other electrodes of the plurality of electrodes.

6. The beam position monitor of claim 1, wherein each electrode of the plurality of electrodes is associated with a plurality of current thresholds.

7. The beam position monitor of claim 6, wherein the beam position monitor is configured to transmit a signal to a control system when a measured current by adjacent electrodes of the plurality of electrodes exceeds a lower threshold of the plurality of current thresholds associated with each electrode of the adjacent electrodes.

8. The beam position monitor of claim 1, wherein each electrode of the plurality of electrodes is associated with an electrode extension distance.

9. The beam position monitor of claim 8, wherein the electrode extension distance represents a distance into the interior of the component that the electrode extends.

10. The beam position monitor of claim 9, wherein each electrode extension distance is adjustable.

11. The beam position monitor of claim 1, wherein the plurality of electrodes are galvanically isolated from the wall of the beam position monitor.

12. The beam position monitor of claim 1, wherein the plurality of electrodes are configured to be biased by an external power supply.

13. The beam position monitor of claim 1, wherein the beam position monitor is configured to transmit a signal to a control system when a beam advancing through the beam line is off axis.

14. The beam position monitor of claim 13, wherein a minimal amount of a beam current of the beam passing through the component of the beam line is reduced due to the plurality of electrodes.

15. The beam position monitor of claim 1, wherein the plurality of electrodes are configured to be biased relative to a wall of the beam position monitor.

16. The beam position monitor of claim 1, wherein the beam is a proton beam.

17. A beam system, comprising:
an ion source;
an accelerator;
a target;
a beam position monitor positioned between the tandem accelerator and the target and configured to detect a position or a beam passing through a component of a beam line of the beam system based on halo current of the beam, wherein the beam position monitor comprises a plurality of electrodes extending into an interior of the component of the beam line, wherein each electrode of the plurality of electrodes is configured to collect current measurements based on exposure of the electrode to the halo current of the beam, wherein each electrode of the plurality of electrodes has an elongate shape and a long axis, and wherein the long axis extends into the interior of the component in a direction perpendicular to a wall of the beam position monitor at a position where the electrode is coupled with the wall; and
a control system configured to adjust beam line parameters based on the position of the beam, wherein the beam system is configured for boron neutron capture therapy (BNCT).

18. The beam system of claim 17, wherein the control system comprises at least one processor and at least one memory storing instructions that, when executed by the at least one processor, cause the control system to:
receive one or more signals from the beam position monitor; and
based on the one or more signals, transmit instructions to discontinue operation of the beam system.

19. The beam system of claim 17, wherein the control system comprises at least one processor and at least one memory storing instructions that, when executed by the at least one processor, cause the control system to:
receive one or more signals from the beam position monitor; and
based on the one or more signals, transmit data representative of the one or more signals to a computing device.

20. The beam system of claim 17, wherein the control system comprises at least one processor and at least one memory storing instructions that, when executed by the at least one processor, cause the control system to:
receive one or more signals from the beam position monitor;
based on the one or more signals, determine that the beam is off a desired axis; and
transmit adjustment signals to one or more beam line components to adjust the position of the beam such that it returns to the desired axis.

21. The beam system of claim 17, wherein the control system comprises at least one processor and at least one memory storing instructions that, when executed by the at least one processor, cause the control system to:
receive one or more signals from the beam position monitor;
based on the one or more signals, determine a degree of beam deflection off a desired axis; and
transmit adjustment signals to one or more beam line components to compensate for the degree of beam deflection off the desired axis.

22. The beam system of claim 17, wherein the beam is a proton beam.

23. The beam system of claim 17, further comprising:
an ion source configured to generate ions; and
a pre-accelerator system configured to accelerate ions from the ion source, wherein the accelerator is a tandem accelerator configured to accelerate ions from the pre-accelerator system.

24. The beam system of claim 23, wherein the pre-accelerator system comprises one or more of an electrostatic lens, a pre-accelerator tube, a magnetic focusing elements, or a pumping chamber.

* * * * *

UNITED STATES PATENT AND TRADEMARK OFFICE
CERTIFICATE OF CORRECTION

PATENT NO. : 12,057,243 B2
APPLICATION NO. : 17/006397
DATED : August 6, 2024
INVENTOR(S) : Vekselman et al.

It is certified that error appears in the above-identified patent and that said Letters Patent is hereby corrected as shown below:

In the Claims

Column 25,
Lines 10 and 11, in Claim 17, "the tandem accelerator" should read --the accelerator--.

Signed and Sealed this
Fifth Day of August, 2025

Coke Morgan Stewart
*Acting Director of the United States Patent and Trademark Office*